(12) United States Patent
May et al.

(10) Patent No.: US 6,833,179 B2
(45) Date of Patent: Dec. 21, 2004

(54) TARGETED ELASTIC LAMINATE HAVING ZONES OF DIFFERENT BASIS WEIGHTS

(75) Inventors: Raymond Jeffrey May, Norcross, GA (US); James Marcus Carr, Kaukauna, WI (US); Richard Harry Thiessen, Appleton, WI (US); Lavada Campbell Boggs, Marietta, GA (US); Hannong Rhim, Roswell, GA (US); James Russell Fitts, Jr., Gainesville, GA (US); Adrian Roy Eggen, Appleton, WI (US); Victor Charles Lang, Appleton, WI (US); Kenneth Michael Salter, LaGrange, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 21 days.

(21) Appl. No.: 09/855,189

(22) Filed: May 14, 2001

(65) Prior Publication Data

US 2002/0002021 A1 Jan. 3, 2002

Related U.S. Application Data

(60) Provisional application No. 60/204,321, filed on May 15, 2000.

(51) Int. Cl.[7] .................................................. B32B 5/04
(52) U.S. Cl. .................. 428/212; 428/215; 428/219; 442/181; 442/370; 442/400; 442/402; 156/160; 156/161; 604/385.01; 604/385.24
(58) Field of Search ........................... 428/212, 215, 428/219; 447/181; 442/370, 400, 402, 329; 156/160, 161; 604/385.01, 385.24

(56) References Cited

U.S. PATENT DOCUMENTS

| | | | |
|---|---|---|---|
| 2,206,761 A | 7/1940 | Bergstein | 93/6 |
| 2,266,761 A | 12/1941 | Jackson, Jr. et al. | 154/46 |
| 2,357,392 A | 9/1944 | Francis, Jr. | 18/47.5 |
| 2,464,301 A | 3/1949 | Francis, Jr. | 154/46 |
| 2,483,405 A | 10/1949 | Francis, Jr. | 154/54 |
| 2,957,512 A | 10/1960 | Wade et al. | 154/33.05 |
| 2,957,852 A | 10/1960 | Frankenburg et al. | 260/75 |
| 3,186,893 A | 6/1965 | Mercer | 161/60 |
| 3,338,992 A | 8/1967 | Kinney | 264/24 |
| 3,341,394 A | 9/1967 | Kinney | 161/72 |

(List continued on next page.)

FOREIGN PATENT DOCUMENTS

| | | | |
|---|---|---|---|
| DE | 37 34 963 A1 | 4/1988 | C08L/21/00 |
| EP | 239 080 A2 | 9/1987 | D01F/6/30 |
| EP | 380 781 A2 | 8/1990 | B05C/5/02 |
| EP | 456 885 B1 | 11/1991 | A61F/13/15 |
| EP | 547 497 A2 | 6/1993 | A61F/13/15 |

(List continued on next page.)

OTHER PUBLICATIONS

*Cellular Materials to Composities, Encyclopedia of Polymer Science and Engineering*, vol. 3, pp. 299–300, (1985), John Wiley & Sons.

*Primary Examiner*—Elizabeth M. Cole
(74) *Attorney, Agent, or Firm*—Pauley Petersen & Erickson

(57) ABSTRACT

A targeted elastic laminate material is provided having at least one low tension zone with first filaments having a first basis weight and at least one high tension zone having second filaments with a second basis weight greater than the first basis weight. The second basis weight is greater due to increased average thickness of the second filaments and/or increased frequency of second filaments relative to the first filaments. Methods and modifications of those methods are provided to produce a targeted elastic laminate material according to the preferred embodiments of this invention.

57 Claims, 12 Drawing Sheets

U.S. PATENT DOCUMENTS

| | | |
|---|---|---|
| 3,371,668 A | 3/1968 | Johnson ................. 128/290 |
| 3,391,048 A | 7/1968 | Dyer et al. .................. 161/58 |
| 3,439,085 A | 4/1969 | Hartmann ................. 264/210 |
| 3,449,187 A | 6/1969 | Bobkowicz ................. 156/161 |
| 3,468,748 A | 9/1969 | Bassett ................. 161/122 |
| 3,502,538 A | 3/1970 | Petersen ................. 161/150 |
| 3,502,763 A | 3/1970 | Hartmann ................. 264/210 |
| 3,542,615 A | 11/1970 | Dobo et al. ................. 156/181 |
| 3,575,782 A | 4/1971 | Hansen ................. 161/141 |
| 3,616,129 A | 10/1971 | Sager ................. 161/57 |
| 3,629,047 A | 12/1971 | Davison ................. 161/57 |
| 3,669,823 A | 6/1972 | Wood ................. 161/141 |
| 3,673,026 A | 6/1972 | Brown ................. 156/164 |
| 3,676,242 A | 7/1972 | Prentice ................. 156/62.4 |
| 3,689,342 A | 9/1972 | Vogt et al. ................. 156/167 |
| 3,692,618 A | 9/1972 | Dorschner et al. ............ 161/72 |
| 3,752,613 A | 8/1973 | Vogt et al. ................. 425/80 |
| 3,773,590 A | 11/1973 | Morgan ................. 156/244 |
| 3,802,817 A | 4/1974 | Matsuki et al. ............. 425/66 |
| 3,806,289 A | 4/1974 | Schwarz ................. 425/72 |
| 3,836,416 A | 9/1974 | Ropiequet ................. 161/2 |
| 3,849,241 A | 11/1974 | Butin et al. ................. 161/169 |
| 3,890,184 A | 6/1975 | Morgan ................. 156/244 |
| 3,912,567 A | 10/1975 | Schwartz ................. 156/167 |
| 3,917,448 A | 11/1975 | Wood ................. 8/125 |
| 3,949,130 A | 4/1976 | Sabee et al. ................. 428/192 |
| 3,978,185 A | 8/1976 | Buntin et al. ................. 264/93 |
| 4,013,816 A | 3/1977 | Sabee et al. ................. 428/288 |
| 4,090,385 A | 5/1978 | Packard ................. 72/191 |
| 4,107,364 A | 8/1978 | Sisson ................. 428/196 |
| 4,148,676 A | 4/1979 | Paquette et al. ............ 156/181 |
| 4,209,563 A | 6/1980 | Sisson ................. 428/288 |
| 4,211,807 A | 7/1980 | Yazawa et al. ............. 428/109 |
| 4,239,578 A | 12/1980 | Gore ................. 156/361 |
| 4,241,123 A | 12/1980 | Shih ................. 428/105 |
| 4,259,220 A | 3/1981 | Bunnelle et al. ........ 260/27 BB |
| 4,300,562 A | 11/1981 | Pieniak ................. 128/287 |
| 4,302,495 A | 11/1981 | Marra ................. 428/110 |
| 4,303,571 A | 12/1981 | Jansen et al. ........ 260/33.6 AQ |
| 4,304,234 A | 12/1981 | Hartmann ................. 128/287 |
| 4,310,594 A | 1/1982 | Yamazaki et al. .......... 428/296 |
| 4,319,572 A | 3/1982 | Widlund et al. ............ 128/284 |
| 4,323,534 A | 4/1982 | DesMarais |
| 4,333,782 A | 6/1982 | Pieniak ................. 156/176 R |
| 4,340,563 A | 7/1982 | Appel et al. ................. 264/518 |
| 4,375,446 A | 3/1983 | Fujii et al. ................. 264/518 |
| 4,405,397 A | 9/1983 | Teed ................. 156/164 |
| 4,413,623 A | 11/1983 | Pieniak ................. 604/365 |
| 4,417,935 A | 11/1983 | Spencer ................. 156/80 |
| 4,418,123 A | 11/1983 | Bunnelle et al. ............ 428/517 |
| 4,440,819 A | 4/1984 | Rosser et al. ................. 428/107 |
| 4,490,427 A | 12/1984 | Grant et al. ................. 428/107 |
| 4,496,417 A | 1/1985 | Haake et al. ................. 145/361 |
| 4,507,163 A | 3/1985 | Menard ................. 156/164 |
| 4,525,407 A | 6/1985 | Ness ................. 428/138 |
| 4,543,099 A | 9/1985 | Bunnelle et al. ........ 604/385 A |
| 4,548,859 A | 10/1985 | Kline et al. ................. 428/251 |
| 4,552,795 A | 11/1985 | Hansen et al. ............. 428/110 |
| 4,555,811 A | 12/1985 | Shimalla ................. 2/51 |
| 4,572,752 A | 2/1986 | Jensen et al. ................. 156/64 |
| 4,586,199 A | 5/1986 | Birring ................. 2/401 |
| D284,036 S | 6/1986 | Birring ................. D2/10 |
| 4,606,964 A | 8/1986 | Wideman ................. 428/152 |
| 4,618,384 A | 10/1986 | Sabee ................. 156/205 |
| 4,626,305 A | 12/1986 | Suzuki et al. ................. 156/164 |
| 4,636,419 A | 1/1987 | Madsen et al. ............. 428/131 |
| 4,640,859 A | 2/1987 | Hansen et al. ............. 428/105 |
| 4,652,487 A | 3/1987 | Morman ................. 428/138 |
| 4,656,081 A | 4/1987 | Ando et al. ................. 428/233 |
| 4,657,793 A | 4/1987 | Fisher ................. 428/36 |
| 4,657,802 A | 4/1987 | Morman ................. 428/152 |
| 4,663,220 A | 5/1987 | Wisneski et al. ........... 428/221 |
| 4,666,542 A | 5/1987 | De Jonckheere ............ 156/164 |
| 4,675,068 A | 6/1987 | Lundmark ................. 156/495 |
| 4,683,877 A | 8/1987 | Ersfeld et al. ................. 128/90 |
| 4,687,477 A | 8/1987 | Suzuki et al. ........... 604/385 A |
| 4,692,368 A | 9/1987 | Taylor et al. ............... 428/137 |
| 4,692,371 A | 9/1987 | Morman et al. ............ 428/224 |
| 4,704,116 A | 11/1987 | Enloe ................. 604/385 A |
| 4,718,901 A | 1/1988 | Singheimer ............ 604/385 A |
| 4,719,261 A | 1/1988 | Bunnelle et al. ............. 525/97 |
| 4,720,415 A | 1/1988 | Vander Wielen et al. ... 428/152 |
| 4,725,468 A | 2/1988 | McIntyre ................. 428/40 |
| 4,726,874 A | 2/1988 | VanVliet ................. 156/495 |
| 4,734,311 A | 3/1988 | Sokolowski ................. 428/152 |
| 4,734,320 A | 3/1988 | Ohira et al. ................. 428/231 |
| 4,735,673 A | 4/1988 | Piron ................. 156/496 |
| 4,756,942 A | 7/1988 | Aichele ................. 428/102 |
| 4,761,198 A | 8/1988 | Salerno ................. 156/334 |
| 4,762,582 A | 8/1988 | de Jonckheere ............ 156/164 |
| 4,775,579 A | 10/1988 | Hagy et al. ................. 428/284 |
| 4,777,080 A | 10/1988 | Harris, Jr. et al. .......... 428/212 |
| 4,789,699 A | 12/1988 | Kieffer et al. ............. 524/271 |
| 4,801,345 A | 1/1989 | Dussaud et al. ............ 156/164 |
| 4,801,482 A | 1/1989 | Goggans et al. .............. 428/68 |
| 4,803,117 A | 2/1989 | Daponte ................. 428/228 |
| 4,804,577 A | 2/1989 | Hazelton et al. ............ 428/224 |
| 4,826,415 A | 5/1989 | Mende ................. 425/722 |
| 4,842,666 A | 6/1989 | Werenicz ................. 156/161 |
| 4,854,985 A | 8/1989 | Soderlund et al. ............ 156/85 |
| 4,854,989 A | 8/1989 | Singheimer ................. 156/161 |
| 4,863,779 A | 9/1989 | Daponte ................. 428/152 |
| 4,874,447 A | 10/1989 | Hazelton et al. ............ 156/167 |
| 4,883,482 A | 11/1989 | Gandrez et al. ......... 604/385.2 |
| 4,883,549 A | 11/1989 | Frost et al. ................. 156/161 |
| 4,891,258 A | 1/1990 | Fahrenkrug ................. 428/138 |
| 4,892,536 A | 1/1990 | DesMarais et al. ...... 604/385.2 |
| 4,892,903 A | 1/1990 | Himes ................. 524/488 |
| 4,900,619 A | 2/1990 | Ostrowski et al. .......... 428/284 |
| 4,906,507 A | 3/1990 | Grynaeus et al. ........... 428/113 |
| 4,908,247 A | 3/1990 | Baird et al. ................. 428/34.9 |
| 4,910,064 A | 3/1990 | Sabee ................. 428/113 |
| 4,917,696 A | 4/1990 | De Jonckheere ......... 604/385.2 |
| 4,917,746 A | 4/1990 | Kons et al. ................. 156/164 |
| 4,929,492 A | 5/1990 | Carey, Jr. et al. ........... 428/198 |
| 4,938,821 A | 7/1990 | Soderlund et al. ............ 156/85 |
| 4,965,122 A | 10/1990 | Morman ................. 428/225 |
| 4,968,313 A | 11/1990 | Sabee ................. 604/385.2 |
| 4,970,259 A | 11/1990 | Mitchell et al. ............. 524/505 |
| 4,977,011 A | 12/1990 | Smith ................. 428/152 |
| 4,984,584 A | 1/1991 | Hansen et al. ............. 128/898 |
| 4,995,928 A | 2/1991 | Sabee ................. 156/164 |
| 4,998,929 A | 3/1991 | Björksund et al. ....... 604/385.2 |
| 5,000,806 A | 3/1991 | Merkatoris et al. ......... 156/161 |
| 5,002,815 A | 3/1991 | Yamanaka et al. .......... 428/109 |
| 5,060,349 A | 10/1991 | Walton et al. ................. 26/18.6 |
| 5,073,436 A | 12/1991 | Antonacci et al. .......... 428/219 |
| 5,093,422 A | 3/1992 | Himes ................. 525/98 |
| 5,100,435 A | 3/1992 | Onwumere ................. 8/115.55 |
| 5,114,087 A | 5/1992 | Fisher et al. ................. 242/42 |
| 5,147,487 A | 9/1992 | Nomura et al. ............. 156/164 |
| D331,627 S | 12/1992 | Igaue et al. ................. D24/126 |
| 5,169,706 A | 12/1992 | Collier, IV et al. ......... 428/152 |
| 5,169,712 A | 12/1992 | Tapp ................. 428/315.5 |
| 5,186,779 A | 2/1993 | Tubbs ................. 156/161 |
| 5,198,281 A | 3/1993 | Muzzy et al. ................. 428/102 |
| 5,200,246 A | 4/1993 | Sabee ................. 428/109 |
| 5,204,429 A | 4/1993 | Kaminsky et al. .......... 526/308 |
| D335,707 S | 5/1993 | Igaue et al. ................. D24/126 |
| 5,209,801 A | 5/1993 | Smith ................. 156/161 |
| 5,219,633 A | 6/1993 | Sabee ................. 428/109 |

| Patent Number | Date | Inventor | Class |
|---|---|---|---|
| 5,226,992 A | 7/1993 | Morman | 156/62.4 |
| 5,229,191 A | 7/1993 | Austin | 428/198 |
| 5,232,777 A | 8/1993 | Sipinen et al. | 428/364 |
| 5,236,430 A | 8/1993 | Bridges | 604/396 |
| 5,236,770 A | 8/1993 | Assent et al. | 428/198 |
| 5,238,733 A | 8/1993 | Joseph et al. | 428/284 |
| 5,246,433 A | 9/1993 | Hasse et al. | 604/396 |
| D340,283 S | 10/1993 | Igaue et al. | D24/126 |
| 5,259,902 A | 11/1993 | Muckenfuhs | 156/164 |
| 5,260,126 A | 11/1993 | Collier, IV et al. | 428/288 |
| 5,272,236 A | 12/1993 | Lai et al. | 526/348.5 |
| 5,278,272 A | 1/1994 | Lai et al. | 526/348.5 |
| 5,288,791 A | 2/1994 | Collier, IV et al. | 524/505 |
| 5,296,080 A | 3/1994 | Merkatoris et al. | 156/496 |
| 5,304,599 A | 4/1994 | Himes | 525/98 |
| 5,308,345 A | 5/1994 | Herrin | 604/385.2 |
| 5,312,500 A | 5/1994 | Kurihara et al. | 156/62.4 |
| 5,324,580 A | 6/1994 | Allan et al. | 428/284 |
| 5,332,613 A | 7/1994 | Taylor et al. | 428/152 |
| 5,334,437 A | 8/1994 | Zafiroglu | 428/219 |
| 5,334,446 A | 8/1994 | Quantrille et al. | 428/284 |
| 5,336,545 A | 8/1994 | Morman | 428/152 |
| 5,342,469 A | 8/1994 | Bodford et al. | 156/244.22 |
| 5,360,854 A | 11/1994 | Bozich, Jr. | 524/274 |
| 5,366,793 A | 11/1994 | Fitts, Jr. et al. | 428/198 |
| 5,376,198 A | 12/1994 | Fahrenkrug et al. | 156/164 |
| 5,385,775 A | 1/1995 | Wright | 428/284 |
| 5,389,173 A | 2/1995 | Merkatoris et al. | 156/164 |
| 5,393,599 A | 2/1995 | Quantrille et al. | 428/284 |
| 5,405,682 A | 4/1995 | Shawver et al. | 428/221 |
| 5,407,507 A | 4/1995 | Ball | 156/163 |
| 5,411,618 A | 5/1995 | Jocewicz, Jr. | 156/164 |
| 5,413,654 A | 5/1995 | Igaue et al. | 156/161 |
| 5,413,849 A | 5/1995 | Austin et al. | 428/293 |
| 5,415,649 A | 5/1995 | Watanabe et al. | 604/385.2 |
| 5,415,925 A | 5/1995 | Austin et al. | 428/287 |
| 5,425,987 A | 6/1995 | Shawver et al. | 428/284 |
| 5,429,694 A | 7/1995 | Herrmann | 156/164 |
| 5,431,644 A | 7/1995 | Sipinen et al. | 604/385.2 |
| 5,431,991 A | 7/1995 | Quantrille et al. | 428/109 |
| 5,447,462 A | 9/1995 | Smith et al. | 450/122 |
| 5,447,508 A | 9/1995 | Numano et al. | 604/385.2 |
| 5,449,353 A | 9/1995 | Watanabe et al. | 604/385.2 |
| 5,464,401 A | 11/1995 | Hasse et al. | 604/385.1 |
| 5,472,775 A | 12/1995 | Obijeski et al. | 428/220 |
| 5,476,563 A | 12/1995 | Nakata | 156/167 |
| 5,484,645 A | 1/1996 | Lickfield et al. | 428/198 |
| 5,498,468 A | 3/1996 | Blaney | 428/198 |
| 5,500,075 A | 3/1996 | Herrmann | 156/494 |
| 5,514,470 A | 5/1996 | Haffner et al. | 428/246 |
| 5,516,476 A | 5/1996 | Haggard et al. | 264/211 |
| 5,523,146 A | 6/1996 | Bodford et al. | 428/198 |
| 5,531,850 A | 7/1996 | Herrmann | 156/161 |
| 5,534,330 A | 7/1996 | Groshens | 428/198 |
| 5,540,976 A | 7/1996 | Shawver et al. | 428/198 |
| 5,545,158 A | 8/1996 | Jessup | 604/385.2 |
| 5,545,285 A | 8/1996 | Johnson | 156/496 |
| 5,549,964 A | 8/1996 | Shohji et al. | 428/224 |
| 5,569,232 A | 10/1996 | Roe et al. | 604/385.2 |
| 5,575,783 A | 11/1996 | Clear et al. | 604/385.1 |
| 5,576,090 A | 11/1996 | Suzuki | 428/152 |
| 5,582,668 A | 12/1996 | Kling | 156/161 |
| 5,591,152 A | 1/1997 | Buell et al. | 604/385.2 |
| 5,597,430 A | 1/1997 | Rasche | 156/161 |
| 5,624,740 A | 4/1997 | Nakata | 428/204 |
| 5,626,573 A | 5/1997 | Igaue et al. | 604/385.1 |
| 5,628,856 A | 5/1997 | Dobrin et al. | 156/244.18 |
| 5,645,672 A | 7/1997 | Dobrin | 156/244.18 |
| 5,652,041 A | 7/1997 | Buerger et al. | 428/198 |
| 5,660,664 A | 8/1997 | Herrmann | 156/161 |
| 5,669,897 A | 9/1997 | Lavon et al. | 604/385.2 |
| 5,681,302 A | 10/1997 | Melbye et al. | 604/373 |
| 5,683,787 A | 11/1997 | Boich et al. | 428/198 |
| 5,690,626 A | 11/1997 | Suzuki et al. | 604/385.2 |
| 5,693,038 A | 12/1997 | Suzuki et al. | 604/385.2 |
| 5,695,849 A | 12/1997 | Shawver et al. | 428/131 |
| 5,709,921 A | 1/1998 | Shawver | 428/152 |
| 5,720,838 A | 2/1998 | Nakata | 156/167 |
| 5,733,635 A | 3/1998 | Terakawa et al. | 428/198 |
| 5,733,822 A | 3/1998 | Gessner et al. | 442/35 |
| 5,735,839 A | 4/1998 | Kawaguchi et al. | 604/385.2 |
| 5,736,219 A | 4/1998 | Suehr et al. | 428/113 |
| 5,746,731 A | 5/1998 | Hisada | 604/385.2 |
| 5,749,865 A | 5/1998 | Yamamoto et al. | 604/385.2 |
| 5,749,866 A | 5/1998 | Roe et al. | 604/385.2 |
| 5,766,737 A | 6/1998 | Willey et al. | 428/198 |
| 5,769,838 A | 6/1998 | Buell et al. | 604/396 |
| 5,769,993 A | 6/1998 | Baldauf | 156/164 |
| 5,772,649 A | 6/1998 | Siudzinski | 604/386 |
| 5,773,373 A | 6/1998 | Wynne et al. | 442/260 |
| 5,773,374 A | 6/1998 | Wood et al. | 442/328 |
| 5,788,804 A | 8/1998 | Hörsting | 156/440 |
| 5,789,065 A | 8/1998 | Haffner et al. | 428/152 |
| 5,789,328 A | 8/1998 | Kurihara et al. | 442/387 |
| 5,814,176 A | 9/1998 | Proulx | 156/167 |
| 5,817,087 A | 10/1998 | Takabayashi et al. | 604/385.2 |
| 5,830,203 A | 11/1998 | Suzuki et al. | 604/385.2 |
| 5,834,089 A | 11/1998 | Jones et al. | 428/97 |
| 5,836,931 A | 11/1998 | Toyoda et al. | 604/385.2 |
| 5,836,932 A | 11/1998 | Buell et al. | 604/396 |
| 5,876,392 A | 3/1999 | Hisada | 604/385.2 |
| 5,879,776 A | 3/1999 | Nakata | 428/92 |
| 5,882,573 A | 3/1999 | Kwok et al. | 264/510 |
| 5,885,686 A | 3/1999 | Cederblad et al. | 428/107 |
| 5,897,546 A | 4/1999 | Kido et al. | 604/391 |
| 5,899,895 A | 5/1999 | Robles et al. | 604/385.2 |
| 5,902,540 A | 5/1999 | Kwok | 264/555 |
| 5,904,298 A | 5/1999 | Kwok et al. | 239/135 |
| 5,916,206 A | 6/1999 | Otsubo et al. | 604/385.2 |
| 5,941,865 A | 8/1999 | Otsubo et al. | 604/385.2 |
| D414,262 S | 9/1999 | Ashton et al. | D24/126 |
| 5,952,252 A | 9/1999 | Shawver et al. | 442/407 |
| 5,964,970 A | 10/1999 | Woolwine et al. | 156/64 |
| 5,997,521 A | 12/1999 | Robles et al. | 604/385.2 |
| 6,004,306 A | 12/1999 | Robles et al. | 604/385.1 |
| 6,033,502 A | 3/2000 | Coenen et al. | 156/64 |
| 6,045,543 A | 4/2000 | Pozniak et al. | 604/385.1 |
| 6,057,024 A | 5/2000 | Mleziva et al. | 428/114 |
| 6,123,694 A | 9/2000 | Pieniak et al. | 604/385.2 |

FOREIGN PATENT DOCUMENTS

| | | | |
|---|---|---|---|
| EP | 570 980 A1 | 11/1993 | A61F/13/15 |
| EP | 604 731 A1 | 7/1994 | B32B/31/00 |
| EP | 617 939 A2 | 10/1994 | A61F/13/15 |
| EP | 743 052 A2 | 11/1996 | A61F/13/15 |
| EP | 753 292 A2 | 1/1997 | A61F/13/15 |
| EP | 713 546 B1 | 3/1997 | D04H/13/00 |
| EP | 761 193 A2 | 3/1997 | A61F/13/15 |
| EP | 761 194 A2 | 3/1997 | A61F/13/15 |
| EP | 763 353 A2 | 3/1997 | A61F/13/15 |
| EP | 787 474 A1 | 8/1997 | A61F/13/15 |
| EP | 806 196 A2 | 11/1997 | A61F/13/15 |
| EP | 814 189 A1 | 12/1997 | D04H/13/00 |
| EP | 582 569 B1 | 6/1998 | B32B/5/26 |
| EP | 1 013 251 A1 | 6/2000 | A61F/13/15 |
| EP | 547 497 B2 | 7/2000 | A61F/13/15 |
| GB | 2 244 422 B | 3/1994 | A61F/13/15 |
| GB | 2 253 131 B | 10/1994 | A61F/13/72 |
| GB | 2 250 921 B | 6/1995 | A61F/13/15 |
| GB | 2 268 389 B | 7/1996 | A61F/13/15 |
| IL | 92891 | 2/1992 | |
| JP | 3-67646 | 3/1991 | B32B/5/28 |

| | | | | | | | | |
|---|---|---|---|---|---|---|---|---|
| JP | 10075978 | 3/1998 | ............ A61F/13/15 | WO | 98/14156 | 4/1998 | ............ A61F/13/15 |
| WO | 90/03464 | 4/1990 | ............ D04H/1/56 | WO | 98/49988 | 11/1998 | ............ A61F/13/15 |
| WO | 92/16371 | 10/1992 | ............ B32B/31/00 | WO | 98/55062 | 12/1998 | ............ A61F/13/15 |
| WO | 93/15247 | 8/1993 | ............ D04H/1/48 | WO | 99/17926 | 4/1999 | ............. B32B/5/04 |
| WO | 93/17648 | 9/1993 | ............ A61F/13/15 | WO | 99/47590 | 9/1999 | ............. C08J/5/18 |
| WO | 94/09736 | 5/1994 | ............ A61F/13/15 | WO | 99/60969 | 12/1999 | ............ A61F/13/15 |
| WO | 95/03443 | 2/1995 | ............ D04H/13/00 | WO | 99/60970 | 12/1999 | ............ A61F/13/15 |
| WO | 95/04182 | 2/1995 | ............ D04H/13/00 | WO | 99/60971 | 12/1999 | ............ A61F/13/15 |
| WO | 95/16562 | 6/1995 | ............. B32B/5/24 | WO | 00/10500 | 3/2000 | ............ A61F/13/15 |
| WO | 95/34264 | 12/1995 | ............ A61F/13/15 | WO | 00/37003 | 6/2000 | ............ A61F/13/15 |
| WO | 96/23466 | 8/1996 | ............ A61F/13/15 | WO | 00/37005 | 6/2000 | ............ A61F/13/15 |
| WO | 96/35402 | 11/1996 | ............ A61F/13/15 | WO | 01/00053 | 1/2001 | ............ A61F/13/15 |

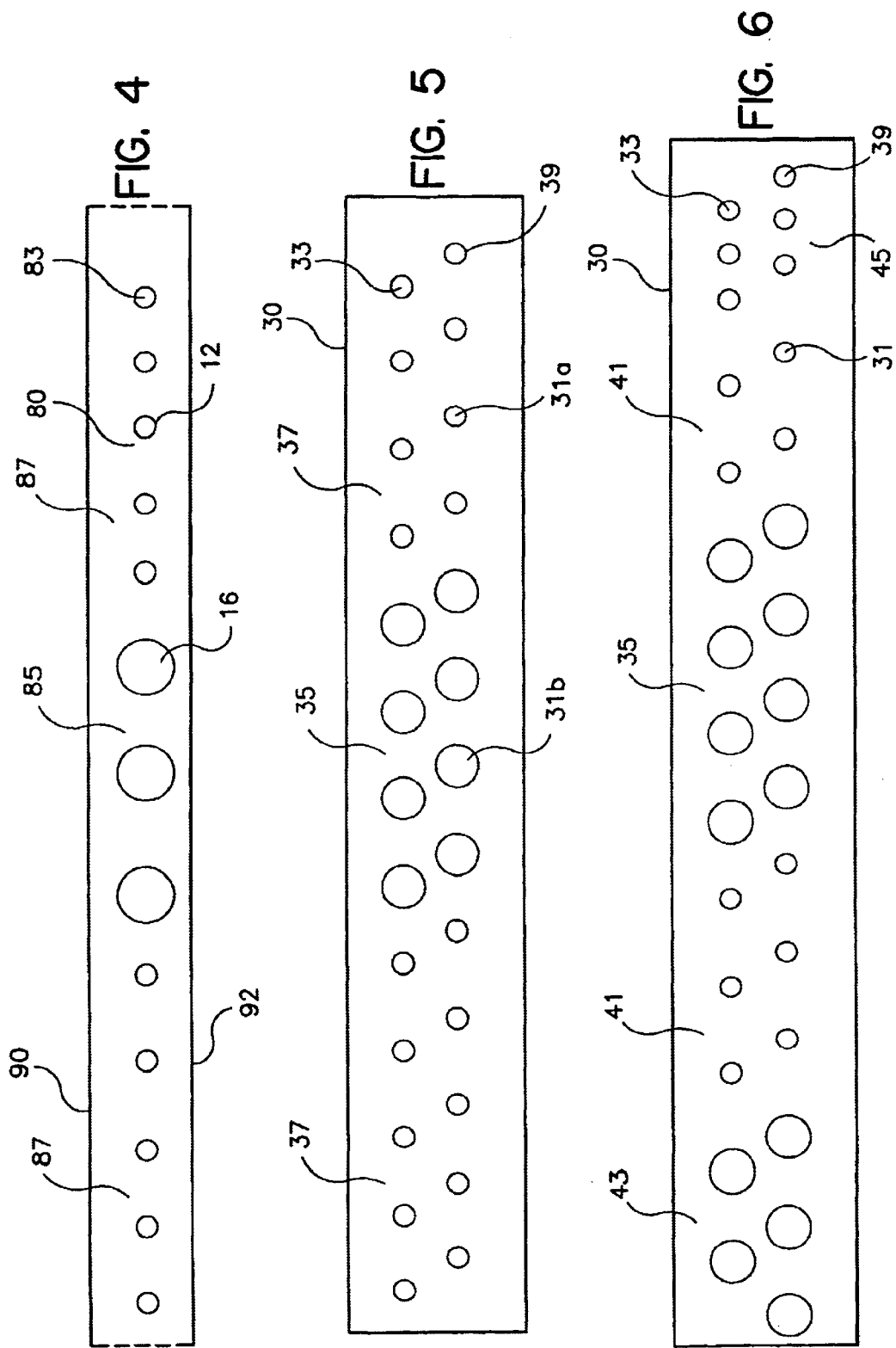

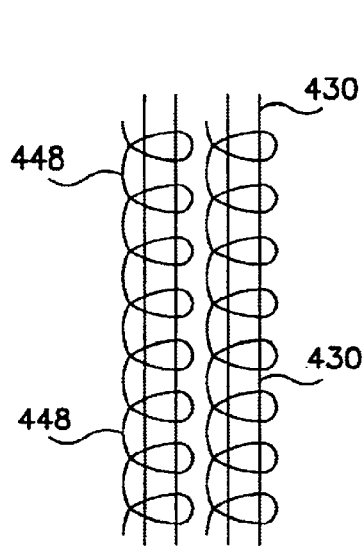 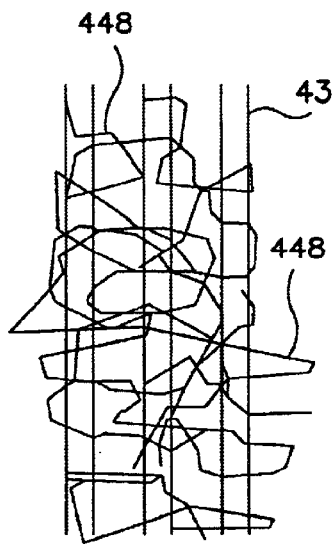 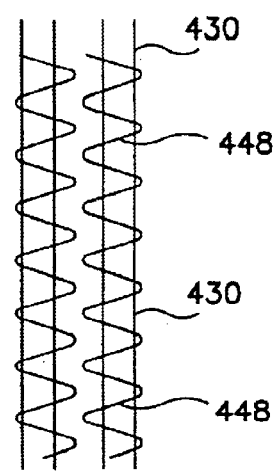
FIG. 16A  FIG. 16B  FIG. 16C
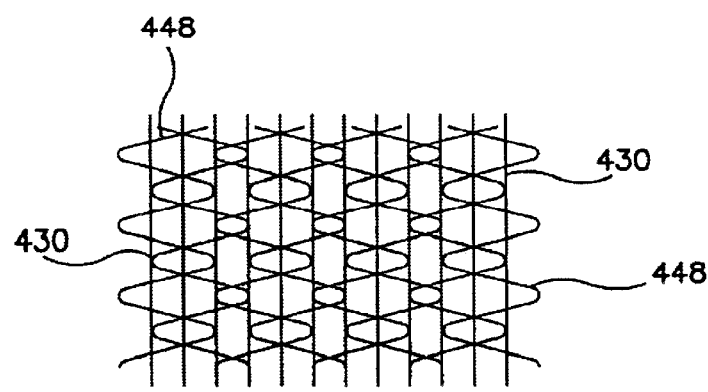
FIG. 16D

TARGETED ELASTIC LAMINATE HAVING ZONES OF DIFFERENT BASIS WEIGHTS

This application claims the benefit of provisional application 60/204,321 filed May 15, 2000.

FIELD OF THE INVENTION

This invention relates to elastic laminate materials having different zones of elastic tension across a width of the material and methods for making the same.

BACKGROUND OF THE INVENTION

Conventional elastic laminates for use in personal care products are composed of a continuous meltblown elastomer web or a series of identical continuous filaments bonded with a meltblown elastomer web. Such conventional stretch-bonded laminate materials exhibit homogeneous tension characteristics across the width of the laminate material. One process for producing a continuous filament stretch-bonded laminate is described in U.S. Pat. No. 5,385,775, issued to Wright, the disclosure of which is incorporated by reference. Additionally, reinforcing filaments have been produced independently of the elastomer spinning process to implement bands having greater tension.

There is a need for a targeted elastic laminate material having at least one low tension zone and at least one high tension zone, having high tension and stretch properties, not requiring separate formation of the high and low tension zones. Additionally, there is a need for a method for producing a targeted elastic laminate material that is easier and less expensive than conventional processes of making stretch-bonded laminate materials.

SUMMARY OF THE INVENTION

The present invention is directed to a targeted elastic laminate (TEL) material having a series of continuous elastomeric filaments bonded to two facing materials. The targeted elastic laminate material has at least one high tension zone having a higher basis weight, and one low tension zone having a lower basis weight, both formed from the same polymer material in the same extrusion step.

The high tension zone and low tension zone can have widths from under 0.5 inch to 50 inches or greater, depending on the processing equipment and the anticipated application. For instance, in a disposable absorbent article, such as training pants, one or more zones of high tension having a width of about 0.5–3 inches, can be produced adjacent to a low tension zone covering the remaining width of the material sheet. The high tension zone may have a tension 1 to 8 times, alternatively about 2 to 4 times, greater than the tension of the low tension zone, at 50% elongation of the fabric.

In one preferred embodiment of this invention, the TEL is made by a vertical filament stretch-bonded laminate (VF SBL) method. In another preferred embodiment, the TEL is made by a continuous filament stretch-bonded laminate (CF SBL) method, which is a modification of the process described in U.S. Pat. No. 5,385,775 to Wright. In either case, a first nonwoven web made from a single polymer or polymer blend contains a first zone of first filaments adjacent a second zone of second filaments, the first and second zones having different average basis weights. The plurality of first filaments are extruded, cooled and stretched to form at least one low tension zone and the plurality of second filaments are extruded, cooled and stretched to form at least one high tension zone. The first and second filaments may be extruded through a single die. To make a stretch-bonded TEL, the filaments are stretched (e.g., uniformly) to about 2 times to about 8 times of their initial length. While the first nonwoven web is in the stretched condition, it is laminated and bonded to at least one, and alternatively two, polymeric layers which have not been stretched. The laminate is allowed to retract, and has different tensions corresponding to the different zones.

In one embodiment of this invention, the VF SBL or CF SBL method is modified to have first and second spinning systems with first and second dies positioned laterally adjacent to each other, to produce a single web having low tension zone filaments and high tension zone filaments of the same elastomeric polymer or polymer blend. The filaments in the high tension zone have a higher basis weight accomplished through larger filaments or higher filament frequency than the filaments in the low tension zone. The second spinnerette used to form the high tension zone has larger extrusion holes, and/or higher hole frequency, than the first spinnerette used to make the low tension zone.

In another embodiment of this invention, the second spinning system is replaced with a set of individually controlled die plates positioned lateral to and/or downstream from the first die. The second spinning system allows placement of the second filaments in between and/or on top of the first filaments to increase the basis weight and tension in a desired fabric zone.

BRIEF DESCRIPTION OF THE DRAWINGS

FIG. 4 is a sectional view of a TEL material in which the nonwoven web contains high and low tension zones accomplished using different filament sizes;

FIGS. 5–6 are bottom plan views of die plates from which the different basis weights causing the high and low tension zones are accomplished via different filament sizes;

FIG. 16A shows a fourth exemplary adhesive spray pattern in a swirled-type of configuration;

FIG. 16B shows a fifth exemplary adhesive spray pattern that is more randomized and which provides a large percentage of adhesive lines in a perpendicular orientation to the elastic filaments;

FIG. 16C illustrates a sixth exemplary adhesive spray pattern having attenuation of adhesive lines in the cross-machine direction;

FIG. 16D shows a seventh exemplary adhesive spray pattern that resembles a "chain-link fence"

DEFINITIONS

Figure 1:
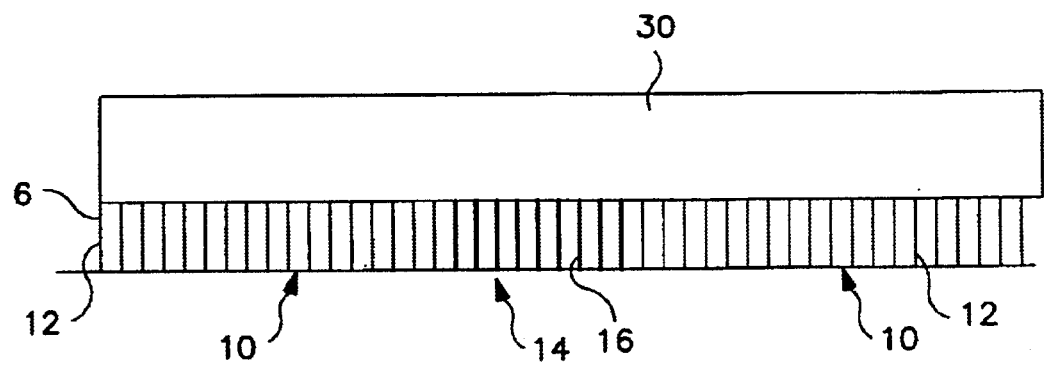
FIG. 1 is a schematic view of an elastic nonwoven layer including a plurality of first filaments forming at least one low tension zone and a plurality of second filaments forming at least one high tension zone extruded from a first die, according to one preferred embodiment of this invention.

The term "targeted elastic laminate" or "TEL" refers to an elastic laminate having at least one elastic nonwoven filament web, in which different zones of different elastic tension exist across a width of the web when the laminate is stretched in a longitudinal direction perpendicular to the width. The different zones may, but do not necessarily, have different elongations at break, or recoveries. What is important is that the different zones exhibit different levels of retractive force when the laminate is uniformly stretched by a selected amount. The elastic nonwoven filament web is laminated to at least one other layer, whereby the laminate exhibits different levels of elastic tension in zones corresponding to the high and low tension zones in the nonwoven filament web.

The term "targeted elastic stretch-bonded laminate" or "TE SBL" refers to a TEL which is formed by stretching the elastic nonwoven filament web having the zones of different elastic tension, maintaining the stretched condition of the elastic nonwoven filament web when the other layer is bonded to it, and relaxing the TEL after bonding.

The term "vertical filament stretch-bonded laminate" or "VF SBL" refers to a stretch-bonded laminate made using a continuous vertical filament process, as described herein.

The term "continuous filament stretch-bonded laminate" or "CF SBL" refers to a stretch-bonded laminate made using a continuous horizontal filament process, as described herein.

The term "elastic tension" refers to the amount of force per unit width required to stretch an elastic material (or a selected zone thereof) to a given percent elongation.

The term "low tension zone" or "lower tension zone" refers to a zone or region in a stretch-bonded laminate material having one or more filaments with low elastic tension characteristics relative to the filament(s) of a high tension zone, when a stretching or biasing force is applied to the stretch-bonded laminate material. Thus, when a biasing force is applied to the material, the low tension zone will stretch more easily than the high tension zone. At 50% elongation of the fabric, the high tension zone may exhibit elastic tension at least 10% greater, suitably at least 50% greater, alternatively about 100–800% greater, or about 150–300% greater than the low tension zone.

The term "high tension zone" or "higher tension zone" refers to a zone or region in a stretch-bonded laminate material having one or more filaments with high elastic tension characteristics relative to the filament(s) of a low tension zone, when a stretching or biasing force is applied to the stretch-bonded laminate material. Thus, when a biasing force is applied to the material, the high tension zone will stretch less easily than the low tension zone. Thus, high tension zones have a higher tension than low tension zones. The terms "high tension zone" and "low tension zone" are relative, and the material may have multiple zones of different tensions.

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, melt-blowing processes, spunbonding processes, air laying processes, and bonded carded web processes. The term also includes films that have been cut into narrow strips, perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the invention are preferably substantially continuous.

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The term "thermoplastic" is meant to describe a material that softens when exposed to heat and which substantially returns to its original condition when cooled to room temperature.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 50 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.50 inches and which, upon being elongated to 1.50 inches and released, will recover to a length of not more than 1.30 inches. Many elastic materials may be stretched by much more than 50 percent of their relaxed length, and many of these will recover to substantially their original relaxed length upon release of the stretching, elongating force. This latter class of materials is generally beneficial for purposes of the present invention.

The term "recover" or "retract" relates to a contraction of a stretched material upon termination of a biasing force following stretching of the material by application of the biasing force.

The term "personal care garment" includes disposable diapers, training pants, swim wear, absorbent underpants, adult incontinence products, and feminine hygiene products. For the purposes of the invention, a baby wipe is considered a personal care garment.

The term "protective garment" includes protective (i.e., medical and/or industrial) disposable gowns, caps, gloves, drapes, face masks, and the like.

The term "disposable garment" includes personal care absorbent garments and protective garments.

The term "series" refers to a set including one or more elements.

DETAILED DESCRIPTION OF THE PRESENTLY PREFERRED EMBODIMENTS

In accordance with the invention, a targeted elastic laminate material (TEL) is provided. As shown in FIG. 1, the TEL includes an elastic nonwoven layer 6 including at least one low tension zone 10 having a plurality of elastomeric first filaments 12 and at least one high tension zone 14 having a plurality of elastomeric second filaments 16. First filaments 12 and second filaments 16 are suitably made from the same elastomeric polymer or polymer blend (i.e., have substantially the same composition.) The TEL material may have multiple high and low tension zones, and each zone may have a different average elastic tension and a different ultimate elongation. Again, the tension of a material is the amount of force per unit width needed to stretch the material to a given elongation. The ultimate elongation is the ultimate length per unit length that a material can be stretched to without causing permanent deformation.

In one desired embodiment, low tension zone 10 is laterally adjacent to high tension zone 14. As shown in FIG. 1, the plurality of first filaments 12 are extruded from first die 30 to form low tension zone 10. The plurality of second filaments 16 are extruded from first die 30 to form high tension zone 14 laterally adjacent low tension zone 10. In other embodiments, low tension zone 10 and high tension zone 14 are laterally spaced apart from each other. In another embodiment, at least a portion of high tension zone 14 overlaps a portion of low tension zone 10.

Figure 7A:
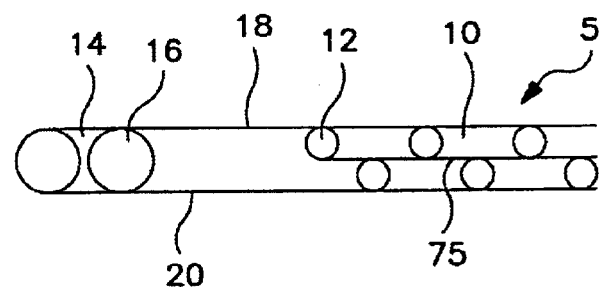
FIGS. 7A and 7B are sectional views of a TEL in which a barrier film is inserted in at least one of the high and low tension zones.
Figure 7B:
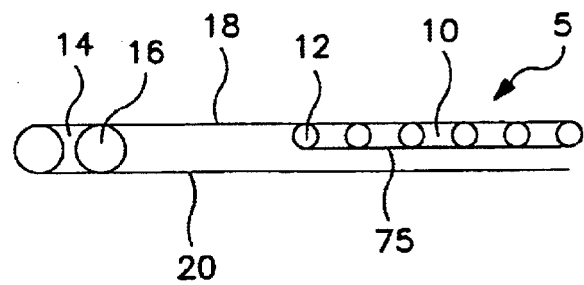

FIGS. 7A and 7B show two embodiments of a TEL material in accordance with the invention. Several examples of processes that can be used to make the TEL material are illustrated in FIGS. 8–12 and 17. As shown in FIGS. 7A and 7B, TEL 5 may include a first facing material 18 bonded to a first side of first filaments 12 forming a low tension zone 10 and second filaments 16 forming a high tension zone 14. TEL 5 may also include an opposing second facing material 20 bonded to a second side of first filaments 12 forming a low tension zone 10 and second filaments 16 forming a high tension zone 14. Each of first facing material 18 and second facing material 20 may comprise a nonwoven web, for example a spunbonded web or a meltblown web, a woven web, or a film. First facing material 18 and second facing material 20 may be formed using conventional processes, including the spunbond and meltblowing processes described in the above "DEFINITIONS." For example, the facing materials may include a spunbonded web having a basis weight of about 0.1–4.0 osy, suitably 0.2–2.0 osy, or about 0.4–0.6 osy. First facing material 18 and second facing material 20 may comprise the same or similar material or different material.

Desirably, first facing material 18 and second facing material 20 are bonded to first filaments 12 and second filaments 16 by an adhesive, for example an elastomeric adhesive such as Findley H2525A, H2525 or H2096. Other bonding means well known to those having ordinary skill in the art may also be used to bond first facing material 18 and second facing material 20 to filaments 12 and 16 including thermal bonding, ultrasonic bonding, mechanical stitching and the like.

In one embodiment of this invention, a barrier film 75, suitably a polymer film, more suitably a polyolefin film such as a polyethylene film, may be positioned between layers of first filaments 12 and/or second filaments 16 (FIG. 7A), and/or between a layer of first filaments 12 and/or second filaments 16 and first facing material 18 and/or second facing material 20 (FIG. 7B).

Figure 2:
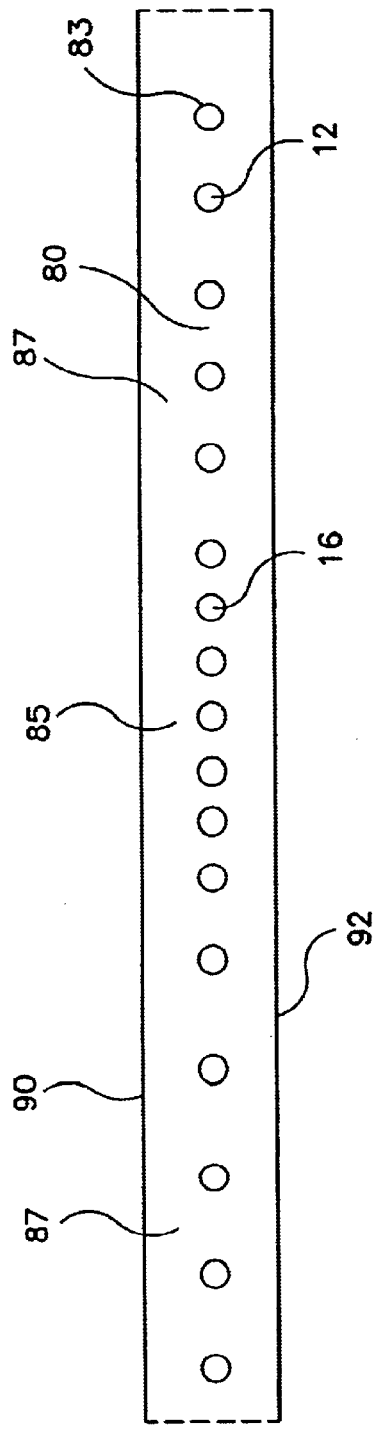
FIG. 2 is a sectional view of a TEL material in which the nonwoven web contains high and low tension zones accomplished using different filament densities.

FIGS. 2–6 illustrate the various TEL laminates and die arrangements useful for preparing the elastomeric nonwoven web 6. In the laminate of FIG. 2, the nonwoven web 80 includes a plurality of equally sized elastic filaments arranged in a single row 83. In a higher tension region 85 of the web 80, the filaments 16 are substantially uniformly spaced and are relatively close to each other. In two lower tension regions 87 of the web 80, the filaments 12 are substantially uniformly spaced but are further apart from each other. The higher tension region 85 contains filaments 16 having relatively higher density (i.e., relatively higher numbers of filaments per unit cross-sectional area), resulting in higher nonwoven web basis weight and higher elastic tension. The lower tension regions 87 contain filaments 16 having relatively lower density (i.e., relatively fewer filaments per unit cross-sectional area), resulting in lower nonwoven web basis weight and lower elastic tension. The nonwoven web 80 is laminated between facing layers 90 and 92, which can be any of the materials described above. The filaments 12 and 16 may be extruded from different zones of a single die or die arrangement, or from two or more different dies.

Figure 3:
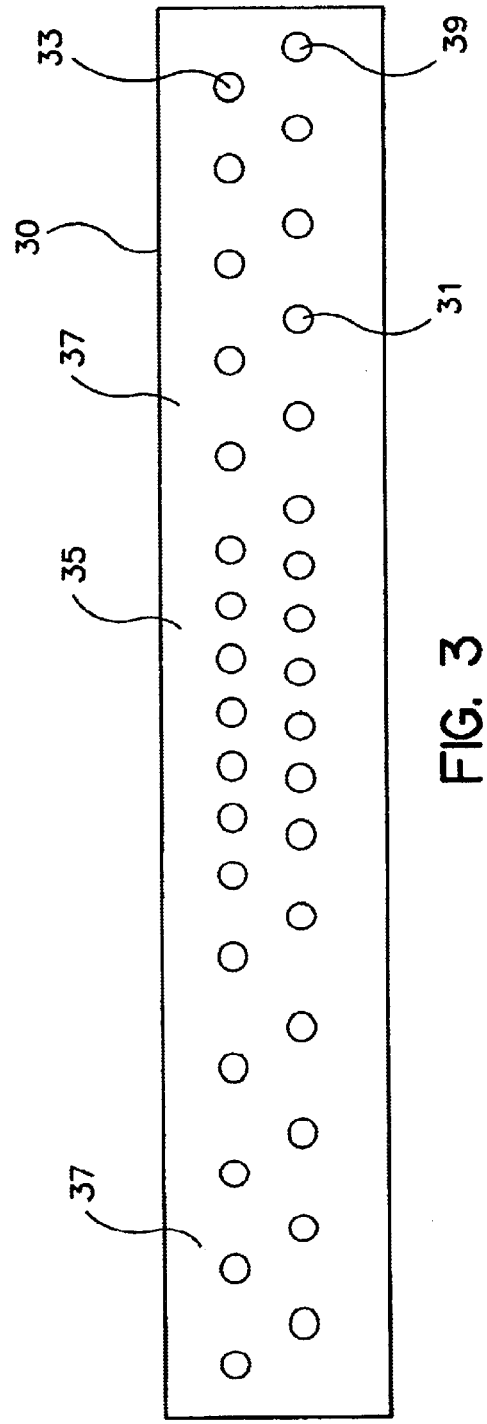
FIG. 3 is a bottom plan view of a die plate from which the different basis weights causing the high and low tension zones are accomplished via different filament densities.

FIG. 3 illustrates an embodiment of die 30 which operates to make a nonwoven web 80 as shown in FIG. 2. In FIG. 3, the die openings 31 are arranged in two rows 33 and 39 instead of one, and are staggered so that individual openings 31 in row 33 are not directly over openings 31 in row 39. When the resulting nonwoven web is contacted with rollers or a conveyor, the extruded filaments may tend to align in a parallel fashion. The die openings 31 have higher frequency in the central region 35 than in end regions 37, corresponding to the desired variations in filament density.

In the laminate of FIG. 4, the web 80 includes a plurality of filaments arranged in a single row 83. In this embodiment, the filaments 16 in the central (high tension) region 85 of the web have a larger size than the filaments 12 in the end (low tension) regions 87. The larger diameter filaments 16 have relatively larger size, resulting in higher nonwoven web basis weight and higher elastic tension. The smaller diameter filaments 12 have relatively smaller size, resulting in lower nonwoven web basis weight and lower elastic tension.

FIG. 5 illustrates an embodiment of die 30 which operates to make a nonwoven web 80 as shown in FIG. 4. In FIG. 5, the die openings 31*a* and 31*b* are arranged in two rows 33 and 39 instead of one, and are staggered so that the individual die openings 31*a* and 31*b* in row 33 are not directly over the openings 31*a* and 31*b* in the row 39. Again, when the resulting nonwoven web is contacted with rollers or a conveyor, the filaments may tend to align in a parallel fashion.

The die of FIG. 6 illustrates how numerous high and low tension zones can be formed in a single nonwoven web. A central region 35 of die 30 includes openings 31 of large diameter, and is used to produce a higher basis weight, higher tension zone. Intermediate zones 41, located on both sides of central region 35, include openings 31 of small diameter with large spaces between them, and are used to produce lower basis weight, lower tension zones. First end zone 43, configured similarly to central region 35 with large diameter die openings, is used to produce a higher basis weight, higher tension zone in the resulting nonwoven web. Second end region 45, configured with lower diameter die openings spaced close together, is also used to produce a higher basis weight, higher tension zone. In summary, zones of higher basis weight and higher elastic tension can be produced in an elastomeric nonwoven web a) using filaments of any diameter but higher nonwoven web density (more filaments per unit cross-sectional area) than in adjacent lower tension zones, and/or b) using filaments of higher diameter than in adjacent zones.

Materials suitable for use in preparing elastomeric first filaments 12 and second filaments 16 herein include diblock, triblock, tetrablock, or other multi-block elastomeric copolymers such as olefinic copolymers, including styrene-isoprene-styrene, styrene-butadiene-styrene, styrene-ethylene/butylene-styrene, styrene-ethylene-propylene-styrene-ethylene-propylene tetrablock, or styrene-ethylene/propylene-styrene, which may be obtained from the Shell Chemical Company, under the trade designation KRATON® elastomeric resin; polyurethanes, including those available from B.F. Goodrich Co., under the trade name ESTANE® thermoplastic polyurethanes; polyamides, including polyether block amides available from Ato Chemical Company, under the trade name PEBAX® polyether block amide; polyesters, such as those available from E.I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®.

A number of block copolymers can be used to prepare thermoplastic elastomeric filaments 12, 16 useful in this invention. Such block copolymers generally comprise an elastomeric midblock portion B and a thermoplastic endblock portion A. The block copolymers may also be thermoplastic in the sense that they can be melted, formed, and resolidified several times with little or no change in physical properties (assuming a minimum of oxidative degradation).

Endblock portion A may comprise a poly(vinylarene), such as polystyrene. Midblock portion B may comprise a substantially amorphous polyolefin such as polyisoprene, ethylene/propylene polymers, ethylene/butylene polymers, polybutadiene, and the like, or mixtures thereof.

Suitable block copolymers useful in this invention include at least two substantially polystyrene endblock portions and at least one substantially ethylene/butylene mid-block portion. A commercially available example of such a linear block copolymer is available from the Shell Chemical Company under the trade designation KRATON® G1657 elastomeric resin. Another suitable elastomer is KRATON® G2760, also available from Shell Chemical Company Other suitable elastomeric polymers may also be used to make thermoplastic elastomeric filaments 12, 16. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

Single-site catalyzed elastomeric polymers (for example, constrained geometry or metallocene-catalyzed elastomeric polymers) are available from Exxon Chemical Company of Baytown, Tex., and from Dow Chemical Company of Midland, Mich. The single-site process for making polyolefins uses a single-site catalyst which is activated (i.e., ionized) by a co-catalyst.

Commercial production of single-site catalyzed polymers is somewhat limited but growing. Such polymers are available from Exxon Chemical Company under the trade name EXXPOL® for polypropylene based polymers and EXACT® for polyethylene based polymers. Dow Chemical Company has polymers commercially available under the name ENGAGE®. These materials are believed to be produced using non-stereo selective single-site catalysts. Exxon generally refers to their single-site catalyst technology as metallocene catalysts, while Dow refers to theirs as "constrained geometry" catalysts under the name INSITE® to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade.

First filaments 12 and second filaments 16 may also contain blends of elastic and inelastic polymers, or of two or more elastic polymers, provided that the blend exhibits elastic properties. First filaments 12 and second filaments 16 may be substantially continuous or staple in length, but are preferably substantially continuous. Substantially continuous filaments have better elastic recovery than staple length filaments. First and second filaments 12, 16 may be circular but may also have other cross-sectional geometries such as elliptical, rectangular, triangular or multi-lobal. In one embodiment, one or more of the filaments may be in the form of elongated, rectangular film strips produced from a film extrusion die having a plurality of slotted openings.

First filaments 12 have a first basis weight and second filaments 16 have a second basis weight greater than the first basis weight. The second basis weight should be at least 10% greater than the first basis weight, suitably at least 50% greater, or 100–800% greater, alternatively 125–500% greater, or as another alternative 200–400% greater. First filaments 12 can have a first basis weight of about 2 grams per square meter (gsm) to about 14 gsm, or about 4 gsm to about 12 gsm, and second filaments 16 can have a second basis weight of about 10 gsm to about 32 gsm, or about 12 gsm to about 30 gsm. Thus, TEL 5 has low tension zone 10 having a first tension and high tension zone 14 having a second tension greater than the first tension.

Elastic tension can be measured, for instance, using an MTS Sintec Model 1/s, available from MTS in Research Triangle Park, N.C., with a cross head speed set to 500 mm/min. Samples having a 3-inch width and 6-inch length can be used, with 3 inches of the length clamped inside the jaws (leaving 3 inches of length for testing). The tension of each high and low tension region can be measured after the portion of the TEL material being tested is held in the extended condition (in the machine direction of the TEL) for 60 seconds.

A standard tensile test can be performed on low tension zone 10 and high tension zone 14 wherein load is measured as a function of elongation. At 50% elongation, high tension zone 14 can have a second tension at least 10% greater, suitably at least 50% greater, or about 100–800% greater, alternatively about 125–500% greater, or as another alternative about 150–300% greater than a first tension of low tension zone 10. Thus, low tension zone 10, when stretched, exhibits less retractive force than high tension zone 14.

Referring again to FIGS. 7A and 7B, the second basis weight of second filaments 16 may be greater than the first basis weight of first filaments 12 as a result of an increase in a diameter of spinning holes 31 in the higher basis weight region, as explained above with respect to FIGS. 4 and 5. The first average thickness (e.g., diameter) of first filaments 12 and the second average thickness (e.g., diameter) of second filaments 16 can be about 0.010 inch to about 0.040 inch, suitably about 0.020 inch to about 0.032 inch. Assuming filaments 12 and 16 have about the same density (expressed as number of filaments per unit cross-sectional area), second filaments 16 should have an average diameter at least 5% higher, suitably at least 20% higher, or 40–300% higher, alternatively 50–125% higher, or as another alternative 75–100% higher than the average diameter of first filaments 12.

Alternatively, as explained with respect to FIGS. 2 and 3, the second basis weight of second filaments 16 can be greater than the first basis weight of first filaments 12 as a result of an increase in frequency of spinning holes 31 in a second spin plate region 37 relative to the frequency of spinning holes 31 in first spin plate region 35. First filaments 12 can have a first frequency and second filaments 16 can have a second frequency of about 4 holes per square inch ("hpi") to about 40 hpi, or about 12 hpi to about 30 hpi. Assuming filaments 12 and 16 have the same diameter, the second frequency should be at least 10% greater, suitably at least 50% greater, or 100–800% greater, alternatively 125–500% greater, or as another alternative 200–400% greater than the first frequency.

Figure 8:
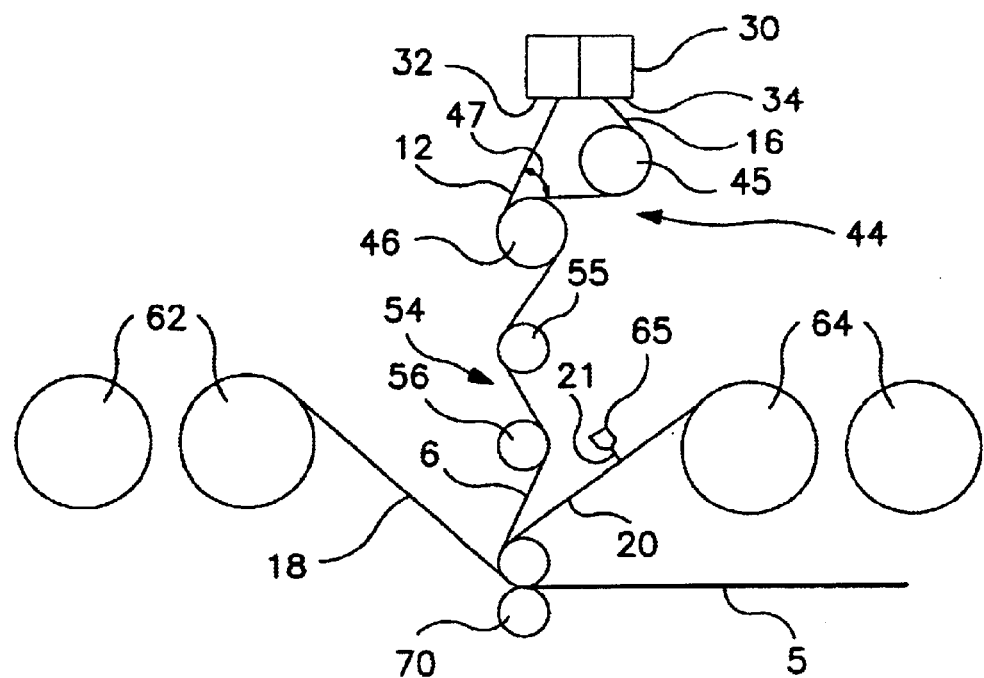
FIG. 8 is a schematic view of one continuous vertical filament process for producing a stretch-bonded TEL material, according to one embodiment of this invention.

In one embodiment of this invention, TEL 5 is produced by a vertical continuous filament stretch-bonded laminate method (VF SBL), as shown in FIGS. 8–10 and 17. Referring to FIG. 8, an extruder (not shown) supplies molten elastomeric material to a first die 30. First die 30 includes different regions of spinning holes tailored to provide the nonwoven fabric 6 with higher and lower zones of elastic tension, having higher and lower basis weights as explained with respect to FIGS. 2–6.

Referring to FIG. 8, molten elastomeric material is extruded from first spin plate region 32 through spinning holes as a plurality of (preferably continuous) elastomeric first filaments 12. Similarly, a plurality of (preferably continuous) elastomeric second filaments 16 of the same polymer material are extruded from second spin plate region 34 through spinning holes of different average diameter and/or frequency. The resulting nonwoven layer 6 has a higher basis weight in the zone defined by second filaments 16, than in the zone defined by first filaments 12. The different basis weights are selected to give the desired different elastic tensions. After extruding first and second filaments 12, 16, first and second filaments 12, 16 are quenched and solidified.

In one embodiment, first and second filaments 12, 16 are quenched and solidified by passing first and second filaments 12, 16 over a first series of chill rolls 44. For instance, first filaments 12 may be contacted with chill roll 46. Second filaments 16, having a higher aggregate basis weight, may be passed over two chill rolls 45 and 46. Any number of chill rolls can be used. Suitably, chill rolls 45 and 46 have a temperature of about 40° F. to about 80° F.

The die of each extruder may be positioned with respect to the first roller so that the continuous filaments meet this first roller at a predetermined angle 47. This strand extrusion geometry is particularly advantageous for depositing a melt extrudate onto a rotating roll or drum. An angled, or canted, orientation provides an opportunity for the filaments to emerge from the die at a right angle to the roll tangent point resulting in improved spinning, more efficient energy transfer, and generally longer die life. This improved configuration allows the filaments to emerge at an angle from the die and follow a relatively straight path to contact the tangent point on the roll surface. The angle 47 between the die exit of the extruder and the vertical axis (or the horizontal axis of the first roller, depending on which angle is measured) may be as little as a few degrees or as much as 90°. For example, a 90° extrudate exit to roller angle could be achieved by positioning the extruder directly above the downstream edge of the first roller and having a side exit die tip on the extruder. Moreover, angles such as about 20°, about 35°, or about 45° away from vertical may be utilized. It has been found that, when utilizing a 12-filament/inch spinplate hole density, an approximately 45° angle (shown in FIG. 8) allows the system to operate effectively. The optimum angle, however, will vary as a function of extrudate exit velocity, roller speed, vertical distance from the die to the roller, and horizontal distance from the die centerline to the top dead center of the roller. Optimal performance can be achieved by employing various geometries to result in improved spinning efficiency and reduced filament breakage. In many cases, this results in potentially increased roll wrap resulting in more efficient energy transfer and longer die life due to reduced drag and shear of the extrudate as it leaves the capillaries of the extruder die and proceeds to the chilled roll.

After first and second filaments 12, 16 are quenched and solidified, first and second filaments 12, 16 are stretched or elongated. In one desired embodiment, first and second filaments 12, 16 are stretched using a first series of stretch rolls 54. First series of stretch rolls 54 may comprise one or more individual stretch rolls 55, suitably at least two stretch rolls 55 and 56, as shown in FIG. 8. Stretch rolls 55 and 56 rotate at a speed greater than a speed at which chill rolls 45 and 46 rotate, thereby stretching the nonwoven layer 6, including the zones of first and second filaments 12, 16.

In one embodiment of this invention, each successive roll rotates at a speed greater than the speed of the previous roll. For example, referring to FIG. 8, chill roll 45 rotates at a speed "x"; chill roll 46 rotates at a speed greater than "x", for example about "1.1x"; stretch roll 55 rotates at a still greater speed, for example about "1.15x"; second stretch roll 56 rotates at a still greater speed, for example about "1.25x" to about "2x"; and a third stretch roll 57 rotates at a still greater speed, for example about "2x" to about "7x." As a result, first and second filaments 12, 16 can be stretched by about 100% to about 800% of an initial pre-stretched length, suitably by about 200% to about 700% of an initial pre-stretched length.

After first and second filaments 12, 16 are stretched, elastic nonwoven web 6 is laminated to a first facing material 18 and (alternatively) a second facing material 20. First facing material 18 is unwound from one of the rollers 62 and laminated to a first side of nonwoven layer 6. Second facing material 20 is unwound from one of the rollers 64 and laminated to a second side of nonwoven layer 6. As shown in FIG. 8, before second facing material 20 is laminated to a second side of elastic nonwoven layer 6, at least a portion of second facing material 20 can be coated or sprayed with an elastomeric adhesive 21, such as Findley H2525A, H2525 or H2096, via an adhesive sprayer 65. The laminate material is then passed through nip rolls 70. The laminate is then relaxed and/or retracted to produce a TEL 5. Other means for bonding the laminate material known to those having ordinary skill in the art may be used in place of nip roll 70.

Figure 9:
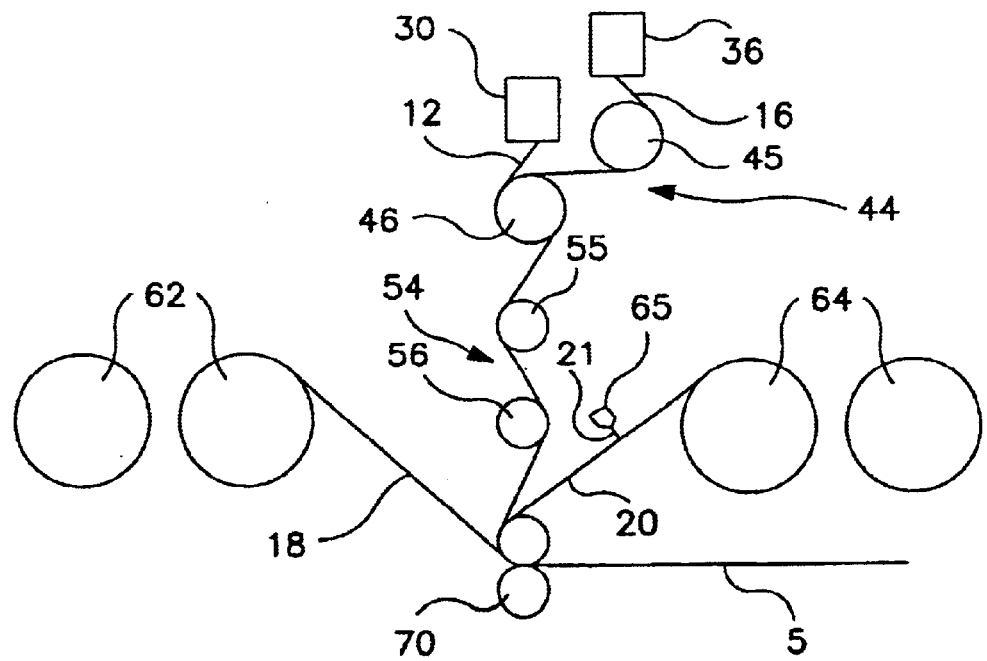
FIG. 9 is a schematic view of another vertical filament process for producing a stretch-bonded TEL material, according to another embodiment of this invention.

FIG. 9 illustrates a VF SBL process similar to that of FIG. 8. In FIG. 9, instead of using a single spinnerette 30 having adjacent die regions for the high and low tension filament zones, two spinnerettes 30 and 36 are employed. First spinnerette 30 extrudes the first filaments 12. Second spinnerette 36 extrudes the second filaments 16. Again, the first and second spinnerettes differ as to the aggregate basis weights of the elastomeric filaments produced. The second spinnerette 36 may have die openings of a) higher frequency and/or b) higher diameter, than the die openings of the first spinnerette 30. Except for the use of two spinnerettes instead of one "hybrid" spinnerette, the processes of FIGS. 8 and 9 are similar. In either case, the first filaments 12 and second filaments 16 ultimately converge to form a single elastic nonwoven layer 6 having zones of higher and lower elastic tensions. The filaments 12 and 16 may converge in a side-by-side fashion as shown in FIG. 1, for instance, to produce at least one lower basis weight, lower tension zone 10 and at least one higher tension, higher basis weight zone 14. Alternatively, the bands of filaments 12 and 16 may have different widths such that a narrower layer or band of second filaments 16 is superimposed directly over a wider layer band of filaments 12, so that the higher tension zone occurs where the two layers coexist. In either process, the first filaments 12 and second filaments 16 may converge as shown, at the chill roll 46.

Figure 10:
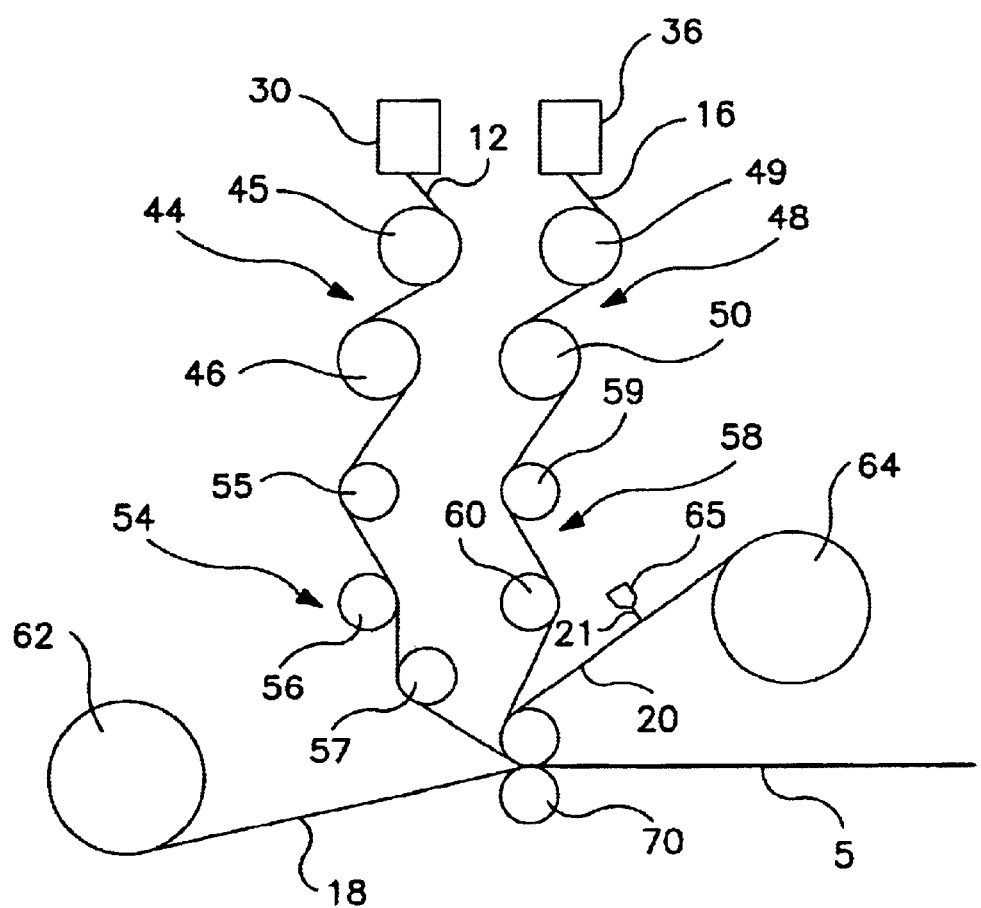
FIG. 10 is a schematic view of another vertical filament process for producing a stretch-bonded TEL material, according to another embodiment of this invention.

FIG. 10 illustrates a VF SBL process in which the second filaments 16 are extruded, cooled and stretched independently from the first filaments 12. First filaments 12 are processed in a manner similar to that described with respect to FIG. 8. First filaments 12 are extruded from spinnerette 30, quenched using chill rolls 45 and 46, and stretched using stretch rolls 55, 56 and 57. Second filaments 16 are processed in parallel fashion (i.e., are extruded from second spinnerette 36), quenched using chill rolls 49 and 50, and stretched using stretch rolls 59 and 60. The first filaments 12 and second filaments 16 converge at the nip rolls 70 to form a nonwoven layer 6 as described above, which is simultaneously laminated between a first facing layer 18 and a second facing layer 20. The resulting laminate is then relaxed and/or retracted to form TEL 5. Except for the separate extrusion cooling and stretching of first and second filaments 12 and 16, the VF SBL process of FIG. 10 is similar to that of FIG. 8. An advantage of the process of FIG. 10 is the possibility of having filaments 12 and 16 stretched by different amounts before lamination to the facing layers.

Figure 17:
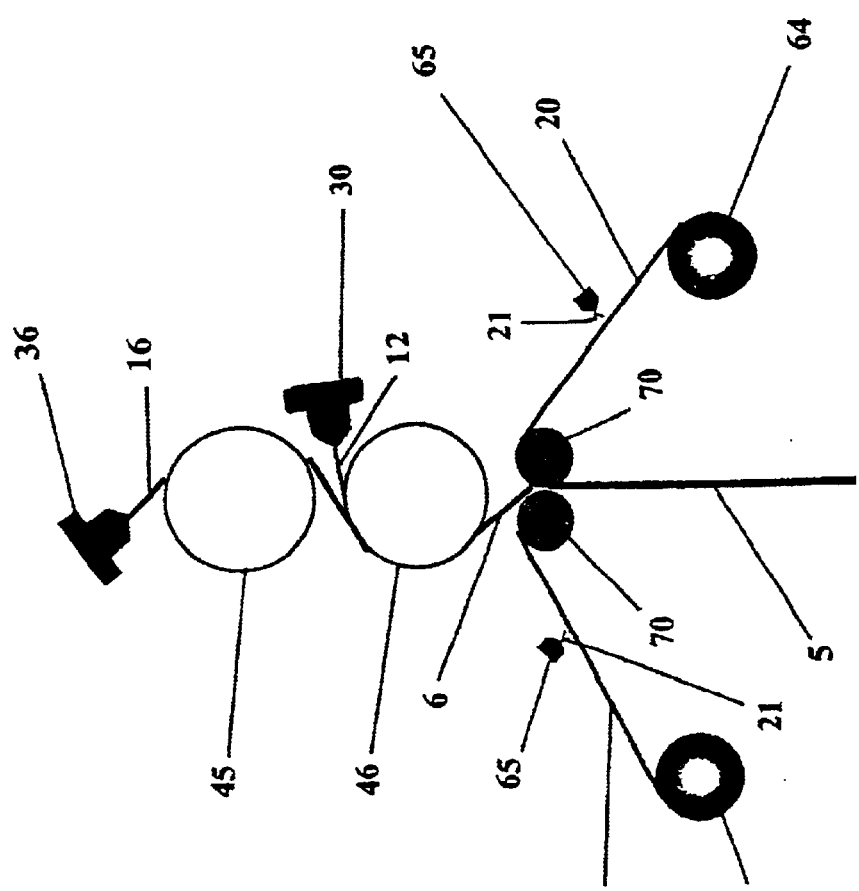
FIG. 17 is a schematic view of another vertical filament process for producing a stretch-bonded TEL material, according to another embodiment of this invention.

FIG. 17 illustrates a VF SBL process in which no stretch rolls 54 are used. Instead, first filaments 12 are extruded onto chill roll 46. Second filaments 16 are extruded onto chill roll 45, where the first filaments 12 and second filaments 16 converge to form a single elastic nonwoven layer 6 having zones of higher and lower elastic tensions. The first and second filaments 12, 16 are stretched between the chill rolls 45, 46 and the nip rolls 70. Except for the lack of stretch rolls 54, the processes of FIGS. 8 and 17 are similar. In either case, the elastic nonwoven layer 6 is laminated between a first facing layer 18 and a second facing layer 20 at the nip rolls 70. The resulting laminate is then relaxed and/or retracted to form TEL 5.

Figure 11:
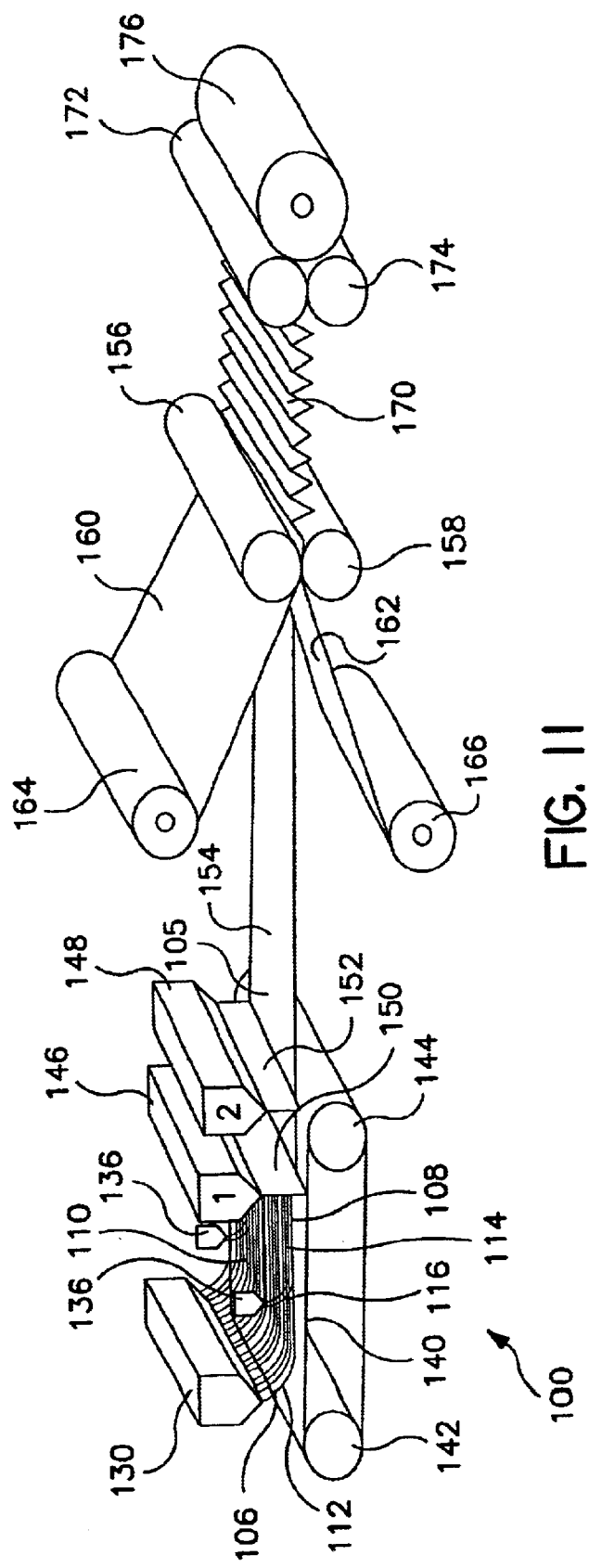
FIG. 11 is a perspective view of a horizontal continuous filament process for producing a stretch-bonded TEL laminate material, according to one embodiment of this invention.

FIG. 11 illustrates a horizontal continuous filament stretch-bond laminate (CF SBL) process 100 for making the TEL of the invention. A first extrusion apparatus 130 (which can be a spinnerette, as described above) is fed with an elastomeric polymer or polymer blend from one or more sources (not shown). In various embodiments, the extrusion apparatus 130 can be configured according to the nonwoven web and die hole arrangements illustrated in FIGS. 2–6 and described above, or similar arrangements, to form a nonwoven layer 106 having similar zones of higher and lower elastic tension. In another embodiment, the extrusion apparatus 130 can be configured with die holes of uniform size and spacing, to yield a nonwoven layer 106 which has uniform elastic tension across its width. The nonwoven layer 106 contains first filaments 112 which are substantially continuous in length. In this regard, the extrusion apparatus 130 may be a spinnerette. Preferably, apparatus 130 is a meltblowing spinnerette operating without the heated gas (e.g., air) stream which flows past the die tip in a conventional meltblowing process. Apparatus 130 extrudes filaments 112 directly onto a conveyor system, which can be a forming wire system 140 (i.e., a foraminous belt) moving clockwise about rollers 142. Filaments 112 may be cooled using vacuum suction applied through the forming wire system, and/or cooling fans (not shown). The vacuum can also help hold the nonwoven layer 106 against the foraminous wire system.

In a desired embodiment, at least one, possibly two or more second extrusion apparatus 136 are positioned downstream of the first extrusion apparatus 130. The second extrusion apparatus create one or more higher tension zones in the nonwoven layer 106 by extruding second filaments 116 of elastic material directly onto the nonwoven layer 106 in bands or zones which are narrower than the width of nonwoven layer 106. The second filaments 116 may be of the same elastic polymer construction as the first filaments 112. The extrusion of second filaments 116 over the first filaments 112 only in selected regions of layer 106, operates to create higher basis weight, higher elastic tension zones 114 where the first and second filaments 112 and 116 coexist, and lower basis weight, lower elastic tension zones 110 where the first filaments 112 exist alone. The first and second filaments 112 and 116 converge, and are combined in the forming conveyor 140 as it travels forward, to yield nonwoven layer 108 having at least one first zone 110 of lower elastic tension, and at least one second zone 114 of higher elastic tension.

As explained above, nonwoven layer 108 can be produced either a) directly from spinnerette 130, which is configured to yield zones of higher and lower basis weight and elastic tension similar to FIGS. 2–6, or b) through the combined effect of spinnerette 130 as a uniform or nonuniform die, and secondary spinnerettes 136 which increase the basis weight and elastic tension in localized regions of layer 108 by extruding secondary filaments 116 onto layer 106. In either case, the nonwoven layer 108 (including filaments 112 and 116) may be incidentally stretched and, to an extent, maintained in alignment by moving the foraminous conveyor 140 in a clockwise machine direction, at a velocity which is slightly greater than the exit velocity of the filaments leaving the die.

To make the TEL 105, the elastic nonwoven layer 108 having higher and lower elastic tension zones is reinforced with one or more elastomeric meltblown layers made of the same or different (preferably the same) elastic polymer material. Referring to FIG. 11, meltblowing extruders 146 and 148 are used to form meltblown layers 150 and 152 onto one side of layer 108, resulting in TEL 105. The meltblown layer or layers may act as structural facing layers in the laminate, and/or may act as adhesive layers if it is desired to add still more layers to the laminate.

Several patents describe various spray apparatuses and methods that may be utilized in supplying the meltblown layers (adhesives) to the outer facing(s) or, when desired, to the elastic strands themselves. For example, the following U.S. patents assigned to Illinois Tool Works, Inc. ("ITW") are directed to various means of spraying or meltblowing fiberized hot melt adhesive onto a substrate: U.S. Pat. Nos. 5,882,573; 5,902,540; 5,904,298. These patents are incorporated herein in their entireties by reference thereto. The types of adhesive spray equipment disclosed in the aforementioned patents are generally efficient in applying the adhesive onto the nonwoven outer facings in the VFL process of this invention. In particular, ITW-brand Dynatec spray equipment, which is capable of applying about 3 gsm of adhesive at a run rate of about 1100 fpm, may be used in the melt-spray adhesive applications contemplated by the present inventive process.

Representative adhesive patterns are illustrated in FIGS. 14A through 16D. Applying an adhesive in a cross-machine pattern such as the ones shown in FIGS. 16C and 16D may result in certain adherence advantages. For example, because the elastic strands are placed in the machine direction, having the adhesive pattern orient to a large degree in the cross-machine direction provides multiple adhesives to elastic crossings per unit length.

In addition, in many particular embodiments of the present invention, the adhesive component is applied to the surface of the nonwoven layer in discrete adhesive lines. The adhesive may be applied in various patterns so that the adhesive lines intersect the elastic filament lines to form various types of bonding networks which could include either adhesive-to-elastic bonds or adhesive-to-elastic bonds, adhesive-to-facing layer, and adhesive-to-adhesive bonds. These bonding networks may include a relatively large total number of adhesive-to-elastic and adhesive-to-adhesive bonds that provide the laminated article with increased strength, while utilizing minimal amounts of adhesive. Such enhancements are achieved by the use of adhesive sprayed onto the surface of the nonwoven in a predetermined and specific pattern. In most cases, a final product with less adhesive exhibits a reduction in undesirable stiffness, and is generally more flexible and soft than products having more adhesive.

Figure 14D:
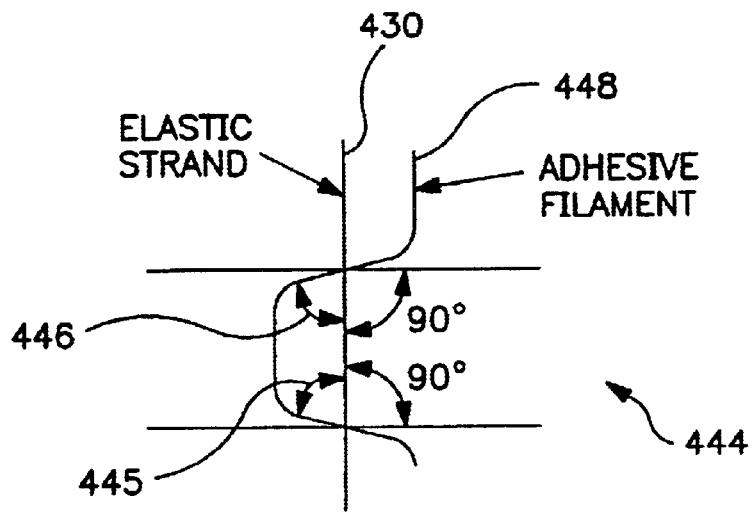
FIG. 14D shows an exemplary bond angle in one exemplary adhesive spray pattern.
Figure 15:
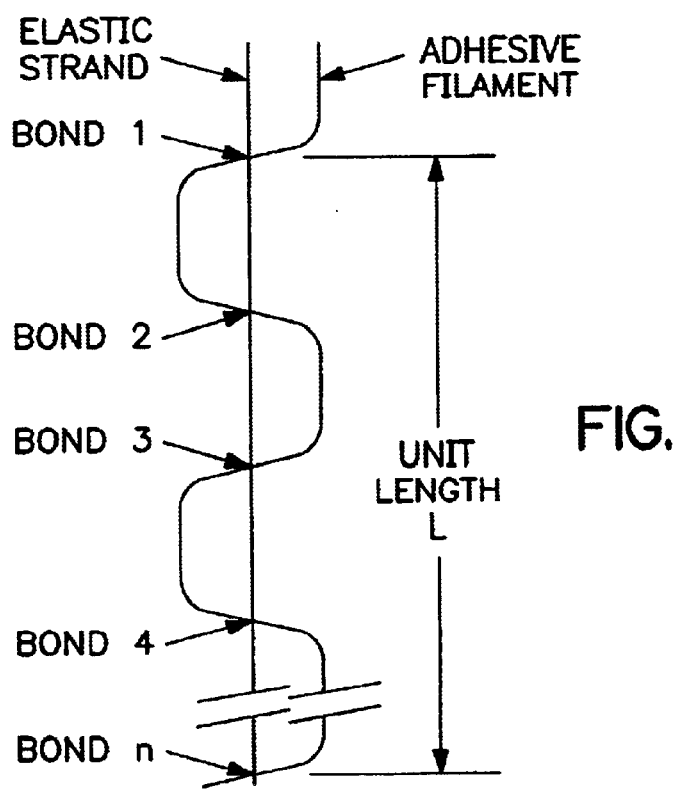
FIG. 15 illustrates the bonding pattern and method of calculating the number of bonds per unit length on elastic strands or filaments.

Applying the adhesive in a pattern so that the adhesive lines are perpendicular or nearly perpendicular to the elastic components has been found particularly advantageous. A true 90° bond angle may not be possible in practice, but an average or mean bond angle that is as great as 50° or 60° will generally produce a suitable bond between the elastic strands and the facing material. A conceptual illustration of these types of bond angles is shown in FIGS. 14D and 15. The adhesive-to-elastic bonds are formed where the lines of adhesive 448 and elastic strands 430 join or intersect.

The continuous adhesive filaments-to-elastic strand intersections are also controlled to a predetermined number of intersections per unit of elastic strand length. By having such adhesive lines in a perpendicular orientation and optimizing the number of bonds per unit of elastic strand length, the final elastic strand laminate can be produced with a minimal amount of adhesive and elastomeric strand material to provide desirable product characteristics at a lower cost.

If the adhesive-to-elastic bonds are too few in number or are too weak, then the elastic tension properties of the laminate may be compromised and the tension applied to the elastic strands may break the adhesive joints. In various known processes, the common remedy for this condition is to increase the number of bonding sites by either increasing the meltspray air pressure, or by slowing the lamination speed. As the meltspray air pressure is increased, the resulting adhesive fiber size is reduced, creating weaker bonds.

Increasing the amount of adhesive used per unit area to create larger adhesive filaments can strengthen these weaker bonds, which usually increases the cost of the laminate. Lowering the lamination speed decreases machine productivity, negatively impacting product cost. The present invention, in part, utilizes an effective bonding pattern where the number of bond sites per length elastic strand are prescribed and where the adhesive-to-elastic strand joints are generally perpendicular in orientation in order to provide maximum adhesive strength. This allows the laminate to be made at minimal cost by optimizing the adhesive and elastomer content to match the product needs.

As used herein, a "scrim" refers generally to a fabric or nonwoven web of material which may be elastic or inelastic, and having a machine direction ("MD") oriented strand component along the path of product flow during manufacture and a cross-machine direction ("CD") strand component across the width of the fabric.

Figure 14A:
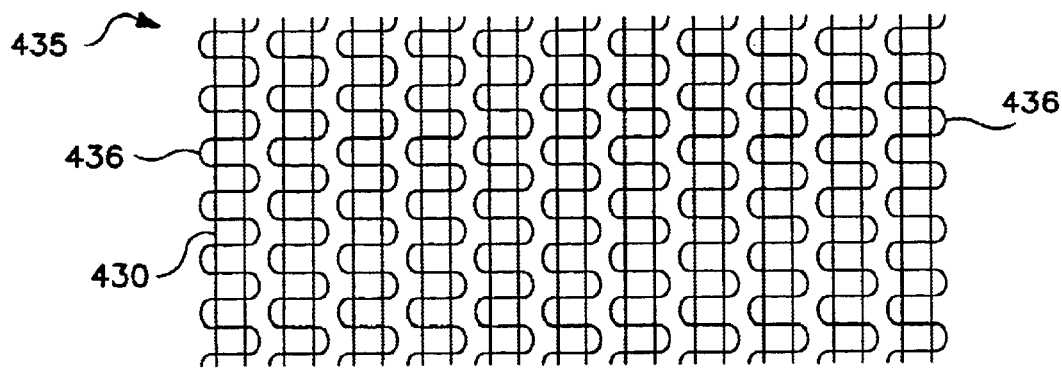
FIG. 14A shows one exemplary adhesive spray pattern in which the adhesive has been applied to the elastic filaments with attenuation in the cross direction.
Figure 14B:
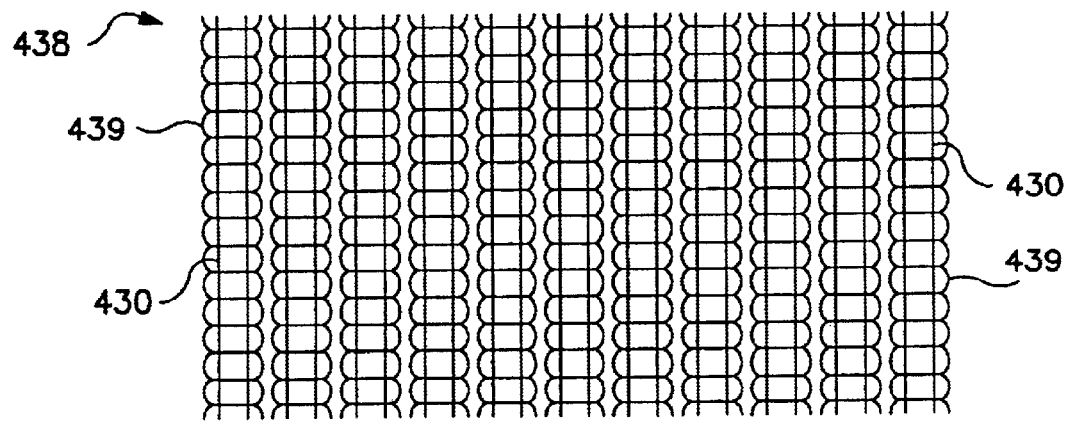
FIG. 14B shows a second exemplary adhesive spray pattern.
Figure 14C:
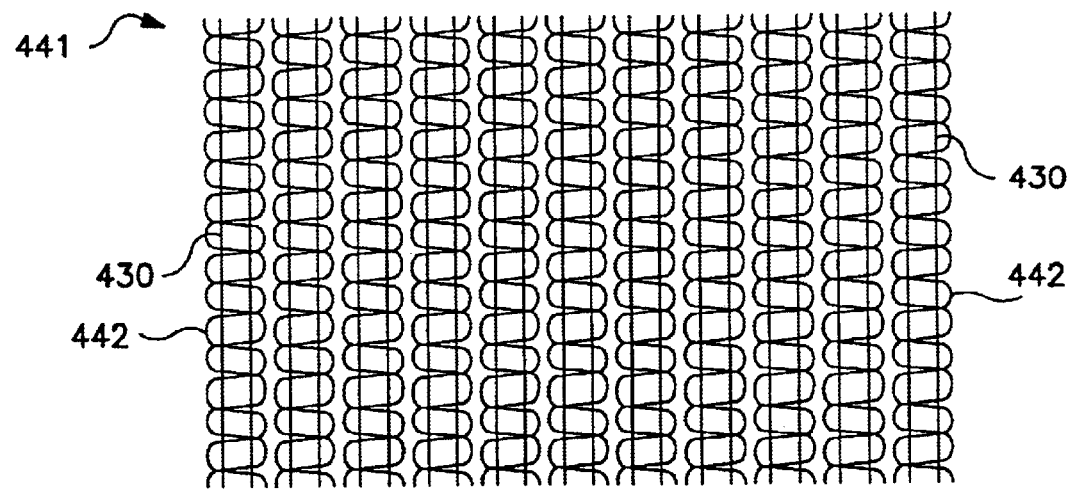
FIG. 14C illustrates a third exemplary adhesive spray pattern.

FIG. 14A shows one exemplary scrim pattern useful in the present invention in which the adhesive has been applied to the elastic filaments with attenuation of the adhesive lines in the cross-machine direction. Scrim pattern 435 includes adhesive lines 436 and elastic filaments 430. FIG. 14B illustrates another exemplary scrim pattern 438 having adhesive lines 439 applied to elastic strands 430. In this embodiment, it can be seen that the bond angle is very high, approaching 90° at the intersection between the adhesive and the elastic filaments. FIG. 14C illustrates still another scrim pattern 441 having adhesive lines 442 and continuous elastic strands 430.

As previously discussed, FIG. 14D illustrates the relatively high bond angle that may be employed in products produced according to the present invention. In particular, lay down angle 444 is shown as the angle formed by the adhesive line 448 and the elastic strand 430. Adhesive/elastic angle 446 and adhesive/elastic angle 445 are shown as being less than 90°.

FIG. 15 utilizes an exemplary bonding pattern to conceptually illustrate the measurement for determining the number of bonds per unit length on elastic strands or filaments. FIG. 16A shows another exemplary bonding pattern having the adhesive-to-adhesive bonding wherein a swirled type of configuration is employed. FIG. 16B illustrates a more randomized pattern wherein a large percentage of adhesive lines are in a perpendicular, or almost perpendicular, orientation to the elastic filaments. FIG. 16C is another exemplary embodiment of a bonding pattern having no adhesive-to-adhesive bonds, but numerous adhesive-to-elastic strand bonds. FIG. 16D illustrates another exemplary bonding pattern that has both adhesive-to-adhesive and adhesive-to-elastic strand bonds. The configuration shown in FIG. 16D is similar to the design of a chain-link fence.

Then, referring back to FIG. 11 for example, if it is desired to convert the TEL 105 into a stretch-bonded laminate, the TEL 105 may be stretched in a stretching stage 154 by pulling it between two nip rolls 156 and 158 which turn at a higher surface speed than the conveyor 140. At the same time, the facing layers 160 and 162 can be unwound from supply rollers 164 and 166, and laminated to the TEL 105 using the stretch roll assembly. To accomplish this dual purpose, the nip rolls 156 and 158 may be smooth or patterned calender rolls which use pressure to bond the materials 160, 105, 162 together as well as stretch the TEL 105. Alternatively, both heat and pressure may be applied to bond the materials 160, 105, 162 together. The resulting stretch-bonded laminate 170 may then be relaxed and/or retracted using nip rollers 172 and 174 that rotate at lower surface speed than calender rolls 158, and may be wound onto storage roll 176. The facing layers 160 and 162 may be any of the facing materials described above, and are suitably polyolefin-based spunbond webs.

Figure 12:
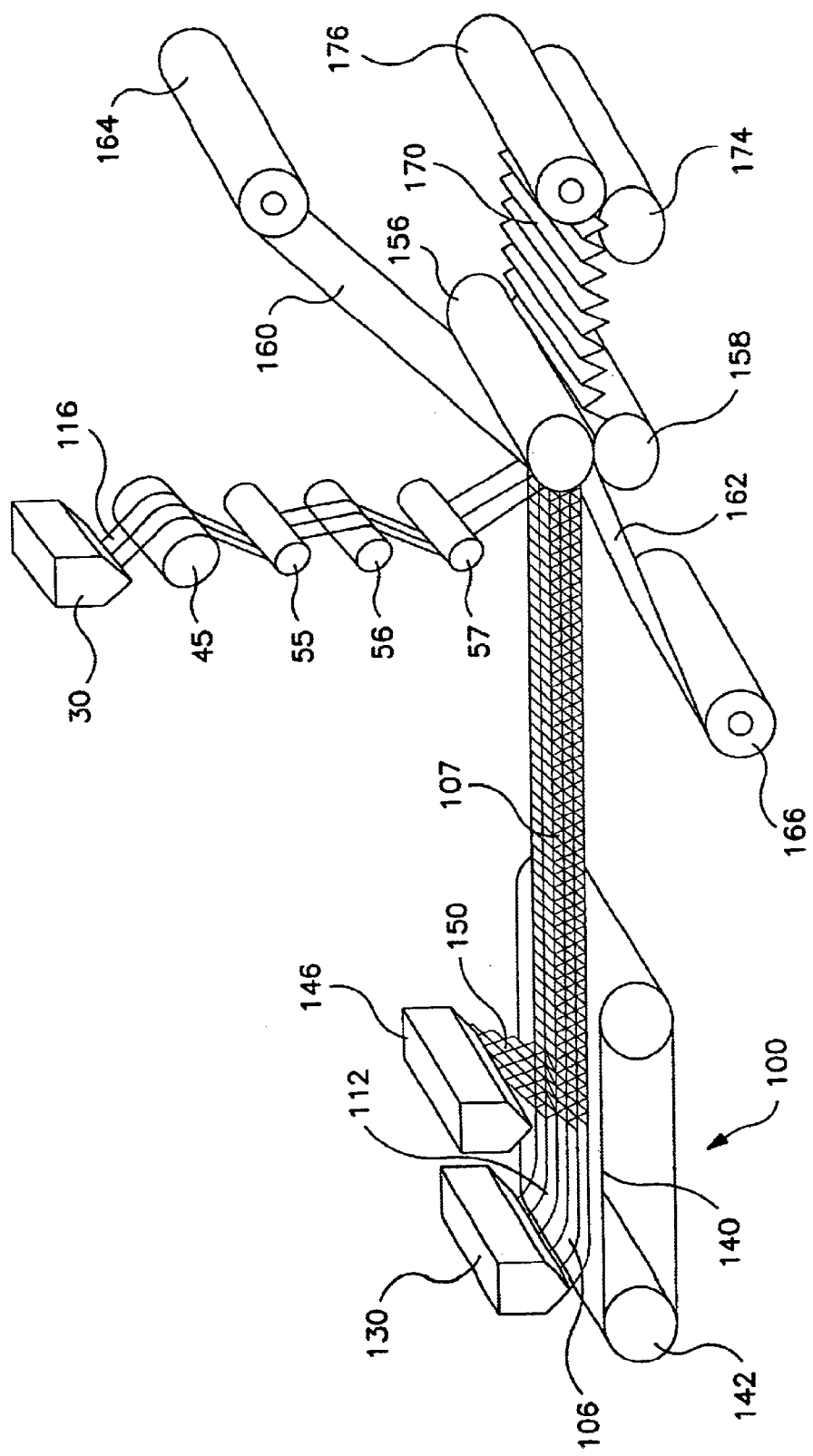
FIG. 12 is a perspective view of a hybrid horizontal continuous filament and vertical filament process for producing a stretch-bonded TEL material.

FIG. 12 illustrates a hybrid of a CF SBL process and a VF SBL process for making a stretch-bonded TEL 170. A first extrusion apparatus 130 is fed with an elastic polymer or polymer blend from one or more sources (not shown). Extrusion apparatus 130 may be any of the various devices described with respect to FIG. 11. Suitably, apparatus 130 is a meltblowing spinnerette operating without the heated gas (e.g., air) stream which flows past the die tip in conventional meltblowing processes. Apparatus 130 extrudes lower tension filaments 112 directly onto a conveyor system, which can be a forming wire system 140 (i.e., a foraminous belt) moving clockwise about rollers 142. Filaments 112 may be cooled using vacuum suction applied through the forming wire system, and/or cooling fans (not shown). The vacuum may also help hold the filaments against the forming wire system.

A meltblowing extruder 146 is used to add a reinforcing elastic meltblown layer 150 to the elastic filaments 112. Suitably, the meltblown layer 150 is made of the same elastic polymer as the low tension filaments 112. The resulting laminate 107 travels forward on the conveyor.

To make the higher tension region, a vertical filament die 30 extrudes higher tension (i.e., higher basis weight) elastic filaments 116 in a band which is narrower than the laminate 107 containing filaments 112. Filaments 116 pass around a chill roll 45, or a series of chill rolls, and a series of stretch rolls, for example three stretch rolls 55, 56 and 57, before being joined with laminate 107 between nip rolls 156 and 158, which are suitably smooth or patterned calender rolls. Simultaneously, facing layers 160 and 162 are unwound from supply rolls 164 and 166 and joined with the laminate between nip rolls 156 and 158 to make TEL 170. As TEL 170 is relaxed, it may assume the puckered configuration shown, due to retraction of high tension filaments 116 present in part of the laminate. TEL 170 may be flattened out between rolls 174 and 176, and wound onto roll 176.

TEL materials made according to the above-described embodiments of this invention can be employed in a wide variety of personal care absorbent garments including, for instance, diapers, training pants, swim wear, absorbent underpants, adult incontinence products, feminine hygiene products, baby wipes, and in protective garments. TEL materials are especially useful in absorbent articles requiring elastic in the waist and/or leg regions of a wearer. TEL materials can also be used in medical garments requiring different levels of tension within an elastic region.

Figure 13:
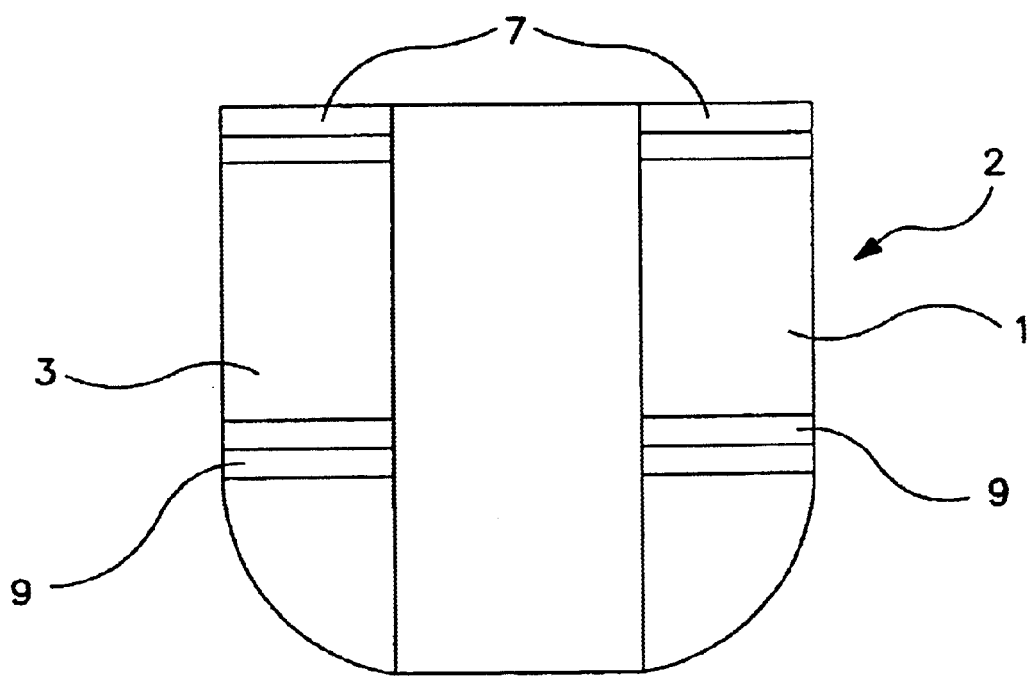
FIG. 13 is a schematic view of an exemplary pant-like absorbent garment with side panels made of a stretch-bonded TEL material having high tension zones and low tension zones, according to one preferred embodiment of this invention.

Referring to FIG. 13, a pant-like absorbent garment 2, such as training pants, includes two side panels 1 and 3 made using a TEL material. Waist elastic regions 7 and leg elastic regions 9 comprise high tension zones while the remaining area of side panels 1 and 3 comprises a low tension zone. During use, the waist elastic regions 7 and the leg elastic regions 9 fit snugly against the wearer and effectively block most spillage of waste material.

EXAMPLE

A roll of TE SBL was produced using the VF SBL method. The TE SBL included a web of continuous filaments laminated between two 0.4 osy polypropylene spunbond facing materials and bonded with Findley H2525A adhesive on one of the facing materials. The filaments of the low tension zone were produced with KRATON® G2760, available from Shell Chemical Co. of Houston, Tex., at a filament density of 8 filaments per inch. The high tension zone was created with the same KRATON® G2760 with the same diameter filaments as the low tension zone but at a 50% increase in filament density of 12 filaments per inch. These filaments were extruded from the same die, quenched over two chill rolls, stretched 4.25 times and laminated between the two facings. The high tension zone had an average tension at 50% elongation of 190 grams per inch. The low tension zone had an average tension at 50% elongation of 130 grams per inch.

While the embodiments of the invention described herein are presently preferred, various modifications and improvements can be made without departing from the spirit and scope of the invention. The scope of the invention is indicated in the appended claims, and all changes that fall within the meaning and range of equivalents are intended to be embraced therein.

What is claimed:

1. A targeted elastic laminate material, comprising:
   at least one low tension zone, the low tension zone including a plurality of elastomeric first filaments, the low tension zone having a first basis weight;
   at least one high tension zone, the high tension zone including a plurality of elastomeric second filaments, the high tension zone having a second basis weight higher than the first basis weight;
   a first facing layer bonded to a first side of the low tension zone and a first side of the high tension zone;
   a second facing layer bonded to a second side of the low tension zone and a second side of the high tension zone; and
   a barrier layer positioned between at least a portion of each of the first and second facing layers.

2. The targeted elastic laminate material of claim 1, wherein the second basis weight is at least 10% greater than the first basis weight.

3. The targeted elastic laminate material of claim 1, wherein the second basis weight is at least 50% greater than the first basis weight.

4. The targeted elastic laminate material of claim 1, wherein the second basis weight is about 100% to about 800% greater than the first basis weight.

5. The targeted elastic laminate material of claim 1, wherein the second basis weight is about 125% to about 500% greater than the first basis weight.

6. The targeted elastic laminate material of claim 1, wherein the second basis weight is about 200% to about 400% greater than the first basis weight.

7. The targeted elastic laminate material of claim 1, wherein the first basis weight is about 2 gsm to about 14 gsm and the second basis weight is about 10 gsm to about 32 gsm.

8. The targeted elastic laminate material of claim 1, wherein the first basis weight is about 4 gsm to about 12 gsm and the second basis weight is about 12 gsm to about 30 gsm.

9. The targeted elastic laminate material of claim 1, wherein the first filaments have a first average thickness and the second filaments have a second average thickness greater than the first average thickness.

10. The targeted elastic laminate material of claim 9, wherein each of the first average thickness and the second average thickness is about 0.010 inch to about 0.040 inch.

11. The targeted elastic laminate material of claim 9, wherein each of the first average thickness and the second average thickness is about 0.020 inch to about 0.032 inch.

12. The targeted elastic laminate material of claim 1, wherein the first filaments have a first frequency and the second filaments have a second frequency higher than the first frequency.

13. The targeted elastic laminate material of claim 12, wherein the first filaments have a first frequency and the second filaments have a second frequency of about 4 hpi to about 40 hpi.

14. The targeted elastic laminate material of claim 12, wherein the first filaments have a first frequency and the second filaments have a second frequency of about 12 hpi to about 30 hpi.

15. The targeted elastic laminate material of claim 1, wherein the low tension zone and the high tension zone are bonded to the facing layer with an elastomeric adhesive.

16. The targeted elastic laminate material of claim 1, wherein the facing layer comprises an elastomeric meltblown web.

17. The targeted elastic laminate material of claim 1, wherein the first elastomeric filaments and the second elastomeric filaments comprise a polymer selected from the group consisting of styrene-isoprene-styrene block copolymers, styrene-butadiene-styrene block copolymers, styrene-ethylene/butylene-styrene block copolymers, styrene-ethylene-propylene-styrene-ethylene-propylene tetrablock copolymers, styrene-ethylene-propylene-styrene block copolymers, polyurethanes, elastomeric polyamides, elastomeric polyesters, elastomeric polyolefin homopolymers and copolymers, atactic polypropylenes, ethylene vinyl acetate copolymers, single-site or metallocene catalyzed polyolefins having a density less than about 0.89 grams/cc, and combinations thereof.

18. The targeted elastic laminate material of claim 1, wherein the first elastomeric filaments and the second elastomeric filaments comprise substantially the same polymer composition.

19. The targeted elastic laminate material of claim 1, wherein the low tension zone is laterally adjacent to the high tension zone.

20. The targeted elastic laminate material of claim 1, wherein each of the first facing layer and the second facing layer comprises a material selected from a nonwoven web, a woven web and a film.

21. The targeted elastic laminate material of claim 1, wherein each of the first facing layer and the second facing layer comprises a spunbond material.

22. The targeted elastic laminate material of claim 1, wherein the low tension zone has a first tension and the high tension zone has a second tension greater than the first tension.

23. A garment comprising the targeted elastic laminate material of claim 1.

24. A method of producing a targeted elastic laminate material, comprising the steps of:
   extruding a plurality of elastomeric first filaments from a plurality of spinning holes in at least one first spin plate region;
   extruding a plurality of elastomeric second filaments from a plurality of spinning holes in at least one second spin plate region, the second filaments having a greater basis weight than a basis weight of the first filaments;
   cooling the first and second filaments;
   stretching the first and second filaments, such that the first filaments are stretched by a different amount than the second filaments;

forming a laminate material by adhering the stretched first and second filaments to a first facing material and an opposing second facing material; and relaxing the laminate material.

25. The method of claim 24, wherein the first and second filaments are stretched by about 100% to about 800% of an initial length.

26. The method of claim 24, wherein the first and second filaments are substantially continuous.

27. The method of claim 24, wherein the first spin plate region has spinning holes with a first diameter and the second spin plate region has spinning holes with a second diameter greater than the first diameter.

28. The method of claim 24, wherein the first spin plate region has a first frequency of spinning holes and the second spin plate region has a second frequency of spinning holes greater than the first frequency.

29. The method of claim 24, wherein the cooling step is accomplished by passing the first and the second filaments over a series of chill rolls.

30. The method of claim 24, wherein the cooling step is accomplished by placing the first and second filaments on a foraminous belt and applying a vacuum through the belt.

31. The method of claim 24, wherein the stretching step is accomplished by passing the first and second filaments over a series of stretch rolls.

32. The method of claim 31, wherein the series of stretch rolls comprises a first stretch roll and a second stretch roll, the first stretch roll rotates at a first speed and the second stretch roll rotates at a second speed greater than the first speed.

33. The method of claim 24, wherein a low tension zone comprises first filaments having a first tension and a high tension zone comprises second filaments having a second tension greater than the first tension.

34. The method of claim 24, wherein the second filaments form a high tension zone that overlaps a portion of a low tension zone formed by the first filaments.

35. A method of producing a targeted elastic laminate material, comprising the steps of:

extruding a plurality of elastomeric first filaments from a first spinning system having at least one first die, the first die having at least one spin plate region with a plurality of first spinning holes;

extruding a plurality of elastomeric second filaments from a second spinning system having at least one second die, the second die having at least one spin plate region with a plurality of second spinning holes, the second filaments having a greater basis weight than a basis weight of the first filaments;

cooling the first and second filaments;

stretching the first and second filaments, such that the first filaments are stretched by a different amount than the second filaments;

forming a laminate material by adhering the stretched first and second filaments to a first facing material and an opposing second facing material; and relaxing the laminate material.

36. The method of claim 35, wherein the first filaments are cooled by placing the first filaments on a foraminous belt and applying a vacuum through the belt, and the second filaments are cooled by passing the second filaments through a series of chill rolls.

37. The method of claim 36, wherein the first filaments are stretched by passing the first filaments through a first series of stretch rolls and the second filaments are stretched by passing the second filaments through a second series of stretch rolls.

38. The method of claim 37, wherein the amount of stretching of the first and second filaments is independently controlled.

39. The method of claim 35, wherein the first filaments are cooled by passing the first filaments through a first series of chill rolls and the second filaments are cooled by passing the second filaments through a second series of chill rolls.

40. The method of claim 39, wherein the first filaments are stretched by passing the first filaments through a first series of stretch rolls and the second filaments are stretched by passing the second filaments through a second series of stretch rolls.

41. The method of claim 40, wherein the amount of stretching of the first and second filaments is independently controlled.

42. The method of claim 35, wherein the second filaments form a high tension zone that overlaps at least a portion of a low tension zone formed by the first filaments.

43. The method of claim 35, further comprising the step of aligning the first filaments and the second filaments during the stretching step.

44. The method of claim 35, wherein a barrier layer is positioned between the first facing material and the second facing material before the laminate material is bonded.

45. The method of claim 35, wherein the first and second filaments are stretched by about 50% to about 300% of an initial length.

46. A disposable garment comprising a targeted elastic laminate material, the targeted elastic laminate material comprising:

at least one low tension zone, the low tension zone having a plurality of elastomeric first filaments, the first filaments having a first basis weight;

at least one high tension zone, the high tension zone having a plurality of elastomeric second filaments, the second filaments having a second basis weight higher than the first basis weight;

a first facing material bonded to a first side of the low tension zone and a first side of the high tension zone;

a second facing material bonded to a second side of the low tension zone and a second side of the high tension zone; and a barrier layer positioned between at least a portion of each of the first and second facing materials.

47. The disposable garment of claim 46, wherein the first and second filaments comprise substantially continuous filaments.

48. The disposable garment of claim 46, comprising a diaper.

49. The disposable garment of claim 46, comprising training pants.

50. The disposable garment of claim 46, comprising swim wear.

51. The disposable garment of claim 46, comprising absorbent underpants.

52. The disposable garment of claim 46, comprising a baby wipe.

53. The disposable garment of claim 46, comprising an adult incontinence product.

54. The disposable garment of claim 46, comprising a feminine hygiene product.

55. The disposable garment of claim 46, comprising a protective garment.

56. The targeted elastic laminate material of claim 1, wherein the barrier layer is positioned between layers including one of elastomeric first filaments, elastomeric second filaments, and combinations thereof.

57. The disposable garment of claim 46, wherein the barrier layer is positioned between layers including one of elastomeric first filaments, elastomeric second filaments, and combinations thereof.

* * * * *